(12) United States Patent
Kondou et al.

(10) Patent No.: US 8,809,427 B2
(45) Date of Patent: Aug. 19, 2014

(54) PHTHALOCYANINE COMPOUND AND PRODUCTION METHOD THEREFOR, AND COLORING COMPOSITION CONTAINING THE PHTHALOCYANINE COMPOUND

(75) Inventors: Hitoshi Kondou, Chiba (JP); Yoshiyuki Sano, Chiba (JP); Yutaka Tachikawa, Chiba (JP)

(73) Assignee: DIC Corporation, Tokyo (JP)

( * ) Notice: Subject to any disclaimer, the term of this patent is extended or adjusted under 35 U.S.C. 154(b) by 208 days.

(21) Appl. No.: 13/389,283

(22) PCT Filed: Aug. 6, 2010

(86) PCT No.: PCT/JP2010/063370
§ 371 (c)(1),
(2), (4) Date: Apr. 20, 2012

(87) PCT Pub. No.: WO2011/018994
PCT Pub. Date: Feb. 17, 2011

(65) Prior Publication Data
US 2012/0232194 A1  Sep. 13, 2012

(30) Foreign Application Priority Data

Aug. 13, 2009  (JP) ................................ 2009-187704
Aug. 31, 2009  (JP) ................................ 2009-199797

(51) Int. Cl.
*C08K 5/3465* (2006.01)
*C08K 5/3447* (2006.01)
(Continued)

(52) U.S. Cl.
USPC ............. 524/88; 540/130; 540/140; 540/142; 544/235; 544/349; 548/306.7; 548/361.5

(58) Field of Classification Search
USPC ............. 524/88; 540/130, 140, 142; 544/235, 544/349; 548/361.5, 306.7
See application file for complete search history.

(56) References Cited

U.S. PATENT DOCUMENTS

| | | | |
|---|---|---|---|
| 6,533,860 B1 | 3/2003 | Hatakeyama et al. | |
| 6,589,330 B2 | 7/2003 | Kato et al. | |

(Continued)

FOREIGN PATENT DOCUMENTS

| | | | |
|---|---|---|---|
| JP | 2001-64534 A | 3/2001 | |
| JP | 2002-194242 A | 7/2002 | |

(Continued)

*Primary Examiner* — Kriellion Sanders
(74) *Attorney, Agent, or Firm* — McDermott Will & Emery LLP

(57) ABSTRACT

Provided is a phthalocyanine compound which is halogen-free and which has a green hue, excellent resistance to organic solvents and acids, and high chroma. Also provided are a metal-free phthalocyanine compound or a metal phthalocyanine compound represented by specified general formula (1-1) or (1-2) and having a N,N'-disubstituted imidazolone structure or piperazinedione structure introduced therein, and a coloring composition including the compound and a synthetic resin. The phthalocyanine compound of the present invention exhibits a clear green color and is halogen-free, and is thus useful as a clear green pigment for coloring materials such as a coating material, plastic, a printing ink, rubber, leather, textile printing, a color filter, a jet ink, a heat transfer ink, etc.

(1-1)

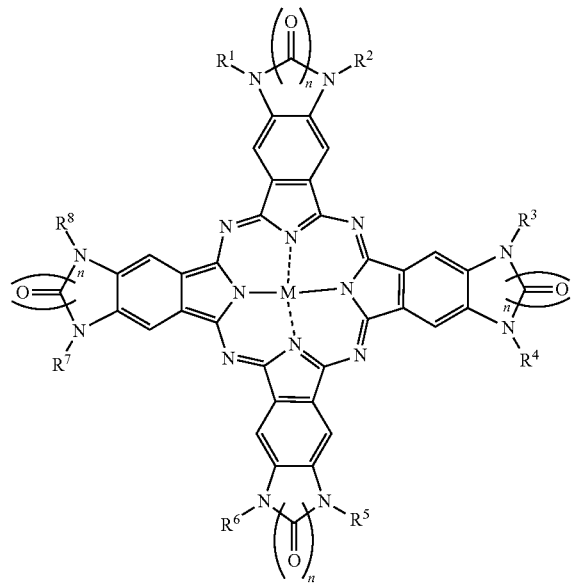

(1-2)

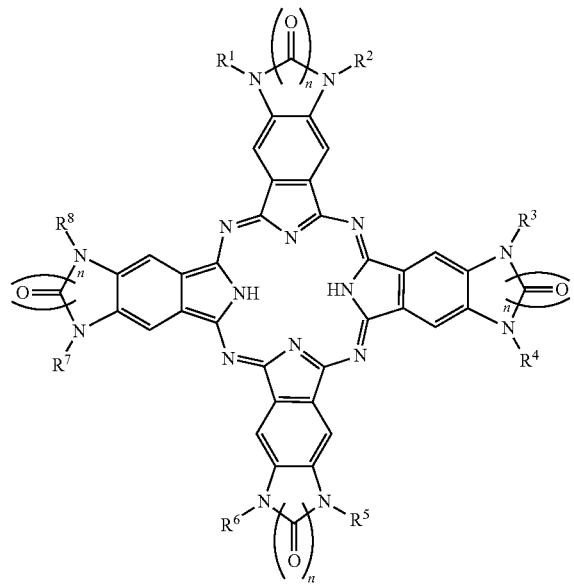

7 Claims, 4 Drawing Sheets

(51) Int. Cl.
*C08K 5/3495* (2006.01)
*C09B 47/04* (2006.01)
*C09B 47/08* (2006.01)
*C09B 67/42* (2006.01)
*C07D 231/56* (2006.01)
*C07D 235/02* (2006.01)
*C07D 237/26* (2006.01)
*C07D 239/70* (2006.01)
*C07D 241/36* (2006.01)
*C07D 241/46* (2006.01)

(56) References Cited

U.S. PATENT DOCUMENTS

| 7,799,911 B2 * | 9/2010 | Nagata | 540/145 |
| 2002/0129740 A1 | 9/2002 | Kato et al. | |
| 2009/0018328 A1 | 1/2009 | Nagata | |

FOREIGN PATENT DOCUMENTS

| JP | 2006-291088 A | 10/2006 |
| JP | 2007-16203 A | 1/2007 |
| WO | WO 2006088140 A1 * | 8/2006 |

* cited by examiner

PHTHALOCYANINE COMPOUND AND PRODUCTION METHOD THEREFOR, AND COLORING COMPOSITION CONTAINING THE PHTHALOCYANINE COMPOUND

CROSS REFERENCE TO PRIOR APPLICATIONS

This application is a U.S. National Phase application under 35 U.S.C. §371 of International Application No. PCT/JP2010/063370, filed on Aug. 6, 2010 and claims benefit of priority to Japanese Patent Application No. 2009-187704, filed on Aug. 13, 2009 and Japanese Patent Application No. 2009-199797, filed on Aug. 31, 2009. The International Application was published in Japanese on Feb. 17, 2011 as WO 2011/018994 A under PCT Article 21(2). The contents of the applications are hereby incorporated by reference.

TECHNICAL FIELD

The present invention relates to a phthalocyanine compound which can be used as a green pigment and a method for producing the same, and a coloring composition containing the phthalocyanine compound.

BACKGROUND ART

Typical green pigments which have been known include polyhalogenated copper phthalocyanine. The polyhalogenated copper phthalocyanine has excellent fastness, but it has recently been concerned about safety and environmental load because it contains a large amount of halogen atoms such as chlorine, bromine, or the like in its molecule. In addition, since the polyhalogenated phthalocyanine contains a large amount of halogen atoms and thus has a high molecular weight and the problem of decreasing coloring strength. Therefore, a pigment capable of green coloring with a compound not containing halogen atoms is required.

As a method for coloring in green with a compound not containing halogen (hereinafter, referred to as "halogen free"), a method of toning to green by mixing copper phthalocyanine as a blue pigment with a yellow organic pigment has been proposed (refer to, for example, Patent Literatures 1 and 2). However, this method has the problem of causing flooding due to mixing of two types of pigments having completely different chemical structures and the problem of causing large hue change due to sunlight exposure because light resistance varies with the types of the pigments mixed.

On the other hand, as a halogen-free compound having a green hue alone, for example, Patent Literature 3 reports a phthalocyanine compound having an imidazolone ring introduced therein, and Patent Literature 4 reports a phthalocyanine compound having a pyrido skeleton introduced therein. The phthalocyanine compound described in Patent Literature 3 assumes a green hue and thus has the property of having no need for toning and the resistance to organic solvents and acids. However, the compound has the problem of low chroma.

CITATION LIST

Patent Literature

PTL 1: Japanese Unexamined Patent Application Publication No. 2001-64534

PTL 2: Japanese Unexamined Patent Application Publication No. 2002-194242

PTL 3: Japanese Unexamined Patent Application Publication No. 2007-16203

PTL 4: Japanese Unexamined Patent Application Publication No. 2006-291088

SUMMARY OF INVENTION

Technical Problem

An object of the present invention is to provide a phthalocyanine compound which is halogen-free and which has a green hue, excellent resistance to organic solvents and acids, and high chroma.

Solution to Problem

As a result of intensive research for resolving the above-described problems, the inventors of the present invention found that a phthalocyanine compound represented by general formula (1-1) or (1-2) described below in which a N,N'-disubstituted imidazolone structure or a piperazinedione structure is introduced is halogen-free and has a green hue, excellent resistance to organic solvents and acids, and high chroma.

The present invention provides a phthalocyanine compound represented by general formula (1-1) or general formula (1-2).

[Chem. 1]

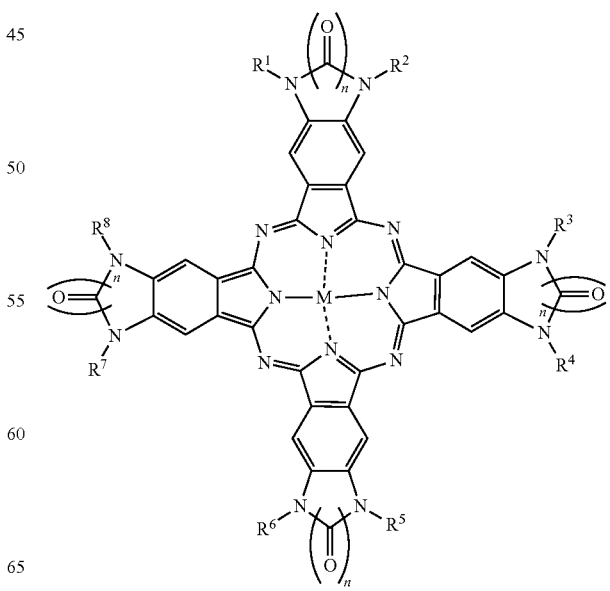

(1-1)

-continued (1-2)

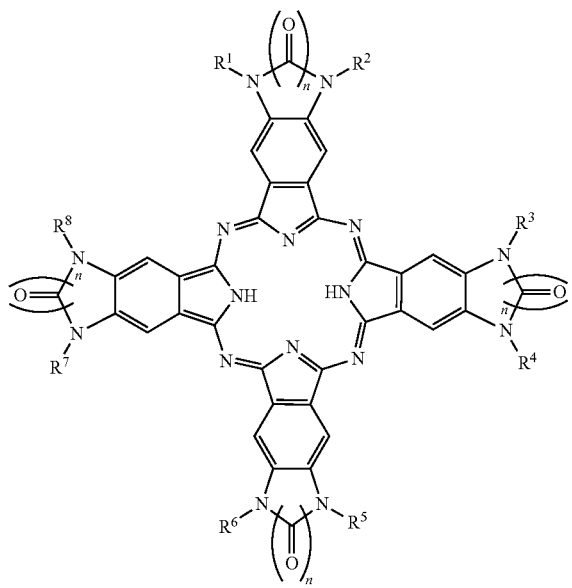

[Chem. 3]

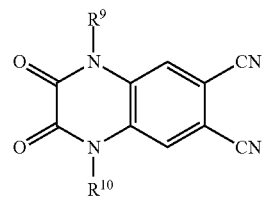

(3)

(In the general formula (3), $R^9$ and $R^{10}$ each independently represent an alkyl group having 1 to 6 carbon atoms or an aralkyl group having 7 to 9 carbon atoms.)

The present invention further provides a method for producing the phthalocyanine compound, the method including thermally condensing the phthalonitrile compound alone represented by the general formula (2) or (3) or a mixture thereof with a metal salt corresponding to the divalent to tetravalent metal atom represented by P in the general formula (1-1).

The present invention further provides a coloring composition containing the phthalocyanine compound and a synthetic resin.

(wherein 1) when n=1, $R^1$ to $R^8$ each independently represent an alkyl group having 1 to 6 carbon atoms or an aralkyl group having 7 to 9 carbon atoms, and 2) when n=2, $R^1$ to $R^8$ each independently represent a hydrogen atom, an alkyl group having 1 to 6 carbon atoms or an aralkyl group having 7 to 9 carbon atoms, and M in the general formula (1-1) represents a divalent to tetravalent metal atom (however, the metal atom may be oxidized)).

The present invention also provides a phthalonitrile compound used as a synthetic raw material for the phthalocyanine compound and represented by general formula (2).

Advantageous Effects of Invention

A phthalocyanine compound of the present invention has a green hue, excellent resistance to organic solvents and acids, and high chroma, and is thus useful as a green pigment. In particular, the compound has a structure in which all benzene rings are substituted with nitrogen-containing rings and thus assumes a green color strongly yellowish. In addition, aggregation little occurs.

The phthalocyanine compound of the present invention is halogen-free and thus has the properties of high safety and low environmental load. Therefore, the compound is very useful as an alternative to a halogenated phthalocyanine pigment which is an existing green pigment for application in which an environmental measure is required.

The phthalocyanine compound of the present invention has the above-described characteristics and thus can be used as a coloring agent for a wide-range of uses such as a printing ink, a coating material, colored plastic, a toner, an ink jet ink, a color filter, etc.

[Chem. 2]

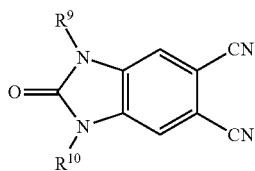

(2)

Figure 1:
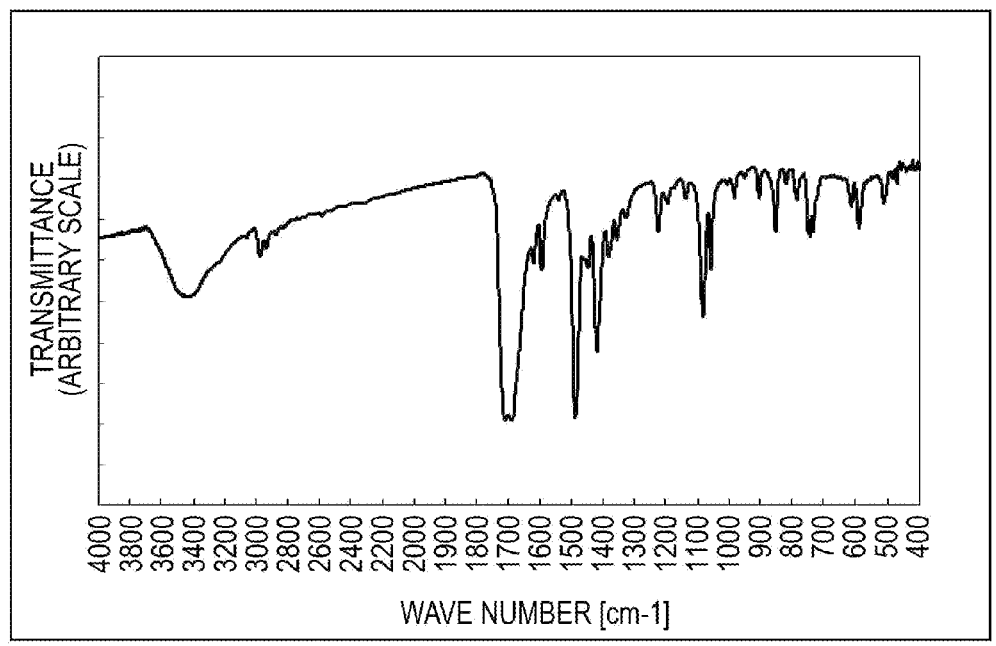
FIG. 1 shows an infrared spectrum of compound (29).
Figure 2:
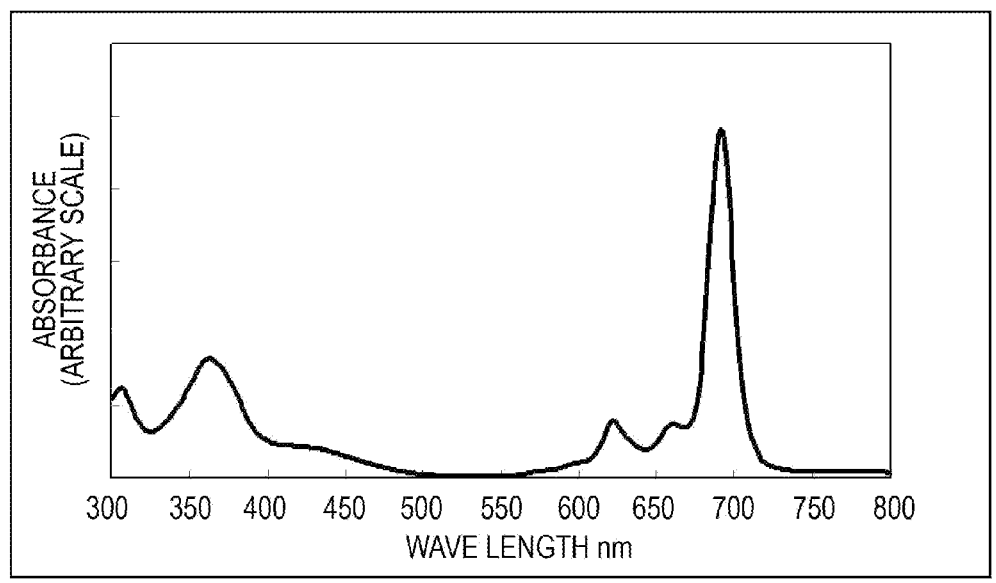
FIG. 2 shows an ultraviolet-visible spectrum of compound (29) in an N-methylpyrrolidin-2-one solution.
Figure 3:
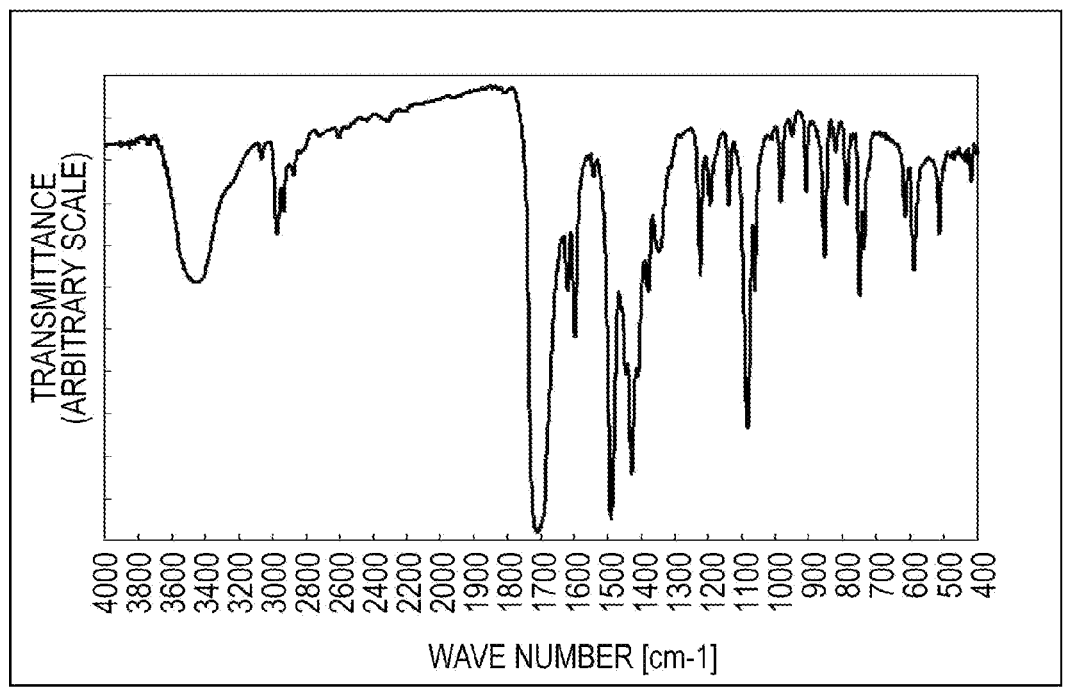
FIG. 3 shows an infrared spectrum of compound (30).
Figure 4:
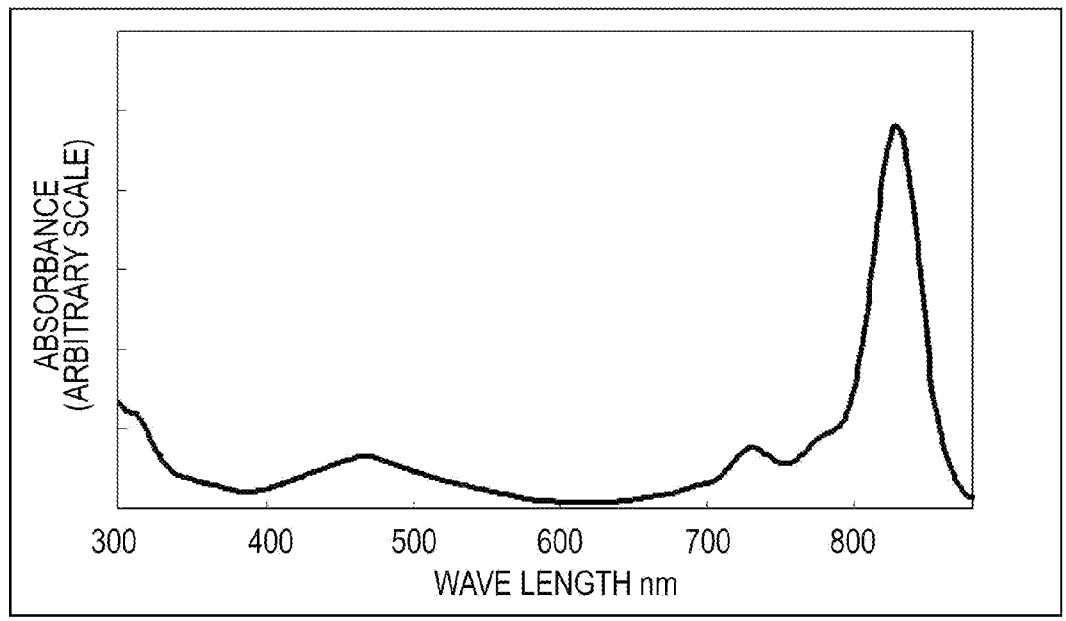
FIG. 4 shows an ultraviolet-visible spectrum of compound (30) in a sulfuric acid solution.

(In the general formula (2), $R^9$ and $R^{10}$ each independently represent an alkyl group having 1 to 6 carbon atoms or an aralkyl group having 7 to 9 carbon atoms.)

The present invention further provides a phthalonitrile compound used as a synthetic raw material for the phthalocyanine compound and represented by general formula (3).

DESCRIPTION OF EMBODIMENTS

A phthalocyanine compound represented by general formula (1-1) or general formula (1-2) of the present invention is a compound having a N,N'-disubstituted imidazolone structure or piperazinedione structure introduced into each of the four benzene skeletons of phthalocyanine. In this application, a compound in which a metal forms a complex at the center of phthalocyanine is represented by the general formula (1-1), and a metal-free compound is represented by the general formula (1-2). Both compounds exhibit a green color.

The phthalocyanine compound represented by the general formula (1-1) is referred to as the "compound (1-1)", and the phthalocyanine compound represented by the general formula (1-2) is referred to as the "compound (1-2)".

A synthesis example of the compound (1-1) or the compound (1-2) of the present invention is described below.

In order to synthesize the compound (1-1) or the compound (1-2), as an intermediate thereof, first a dicyanobenzimidazolone compound represented by general formula (2) below, which is a dinitrile compound having an N,N'-disubstituted imidazolone ring, or a dicyanotetrahydroquinoxalinedione compound represented by general formula (3) below, which is a dinitrile compound having a piperazinedione ring, are synthesized according to a synthesis method described below.

[Chem. 4]

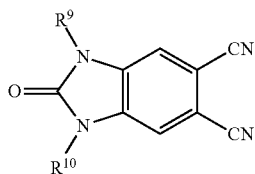

(2)

(In the formula, $R^9$ and $R^{10}$ each independently represent an alkyl group having 1 to 6 carbon atoms or an aralkyl group having 7 to 9 carbon atoms.)

[Chem. 5]

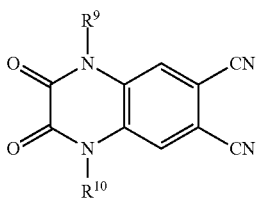

(3)

(In the general formula (3), $R^9$ and $R^{10}$ each independently represent an alkyl group having 1 to 6 carbon atoms or an aralkyl group having 7 to 9 carbon atoms.)

Synthesis of N,N'-disubstituted dicyanobenzimidazolone Compound

A compound having $R^9$ and $R^{10}$ which are the same in the general formula (2) (when $R^9$ and $R^{10}$ are the same, both are denoted by $R^{11}$, and the compound is represented by general formula (6) hereinafter) can be synthesized by, for example, the following method. First, 1,2-diamino-4,5-dicyanobenzene (formula (4) below) is reacted with phosgene, chlorocarbonic acid ester, urea, or 1,1'-carbonylbis-1H-imidazole in an organic solvent, such as acetonitrile or the like, at 0 to 130° C. for 1 to 6 hours, producing a dicyanobenzimidazolone compound (hereinafter referred to as a "compound (5)") represented by general formula (5) below. Then, the compound (5) is reacted with a compound, such as alkyl halide, aralkyl halide, or the like, in an organic solvent, such as N,N-dimethylformamide, N-methyl-2-pyrrolidinone, dimethylsulfoxide, or the like, in the presence of a base such as cesium carbonate, potassium carbonate, potassium tert-butoxide, or the like, producing the compound (6) in which $R^9$ and $R^{10}$ in a N,N'-disubstituted dicyanobenzimidazolone compound (hereinafter referred to as a "compound (2)") represented by the general formula (2) are the same.

[Chem. 6]

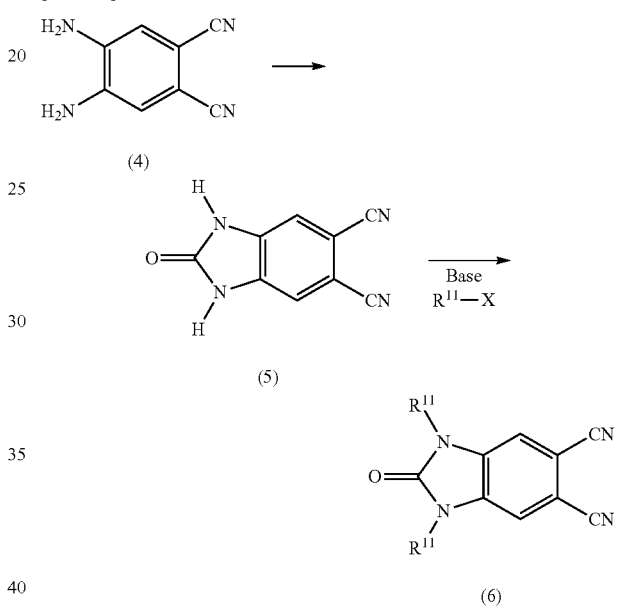

(In the general formula (6), $R^{11}$ represents an alkyl group having 1 to 6 carbon atoms or an aralkyl group having 7 to 9 carbon atoms. In addition, in the reaction formula, X represents a chlorine atom, a bromine atom, an iodine atom, a tosyl group, a mesyl group, or a sulfonate group such as a trifluoromethanesulfonic acid group.)

A synthesis method for 1,2-diamino-4,5-dicyanobenzene is described in Chemistry-A European Journal, 9(5), 1233-(2003), Journal of Organic Chemistry, 71, 3345 (2006), and Synthesis, 1179 (2008).

A compound having $R^9$ and $R^{10}$ which are different in the general formula (2) (when $R^9$ and $R^{10}$ are different, both are denoted by $R^{12}$ and $R^{13}$, and the compound is represented by general formula (12) hereinafter) can be synthesized by, for example, the following method. A compound (8) is produced by substituting, with amine, nitro groups of compound (7) produced by dinitrating the 4- and 5-positions of o-dibromobenzene. Then, the bromine atoms are substituted with cyano groups, and the nitro group is reduced. According to the above-described method, the resultant diamino compound (10) can be converted to the N,N'-disubstituted dicyanobenzimidazolone compound (12) in which $R^9$ and $R^{10}$ in the general formula (2) are different from each other. This synthesis method is described in detail in Chemical Communications, 2236 (2002)

[Chem. 7]

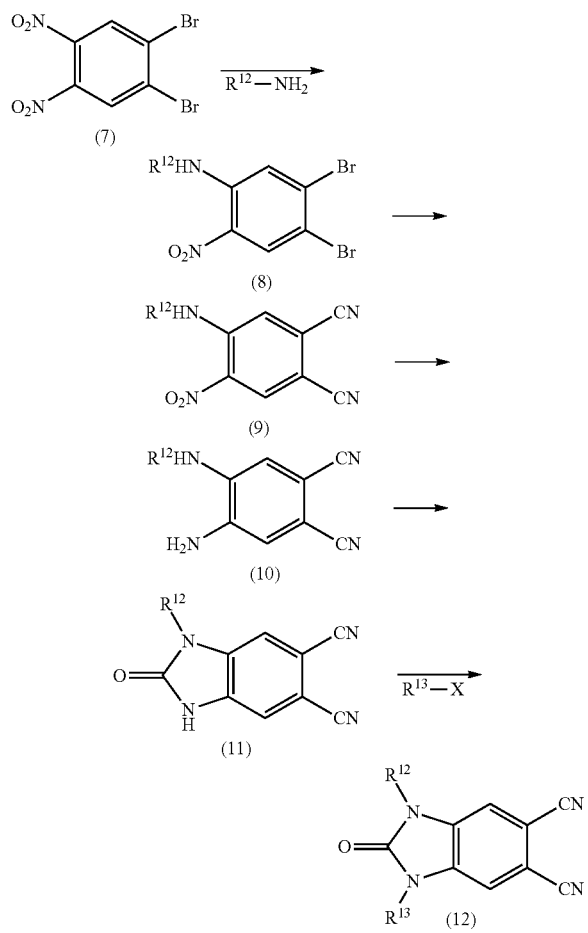

(In the general formula (12), $R^{12}$ and $R^{13}$ each independently represent an alkyl group having 1 to 6 carbon atoms or an aralkyl group having 7 to 9 carbon atoms (excluding a case in which $R^{12}$ and $R^{13}$ are the same group). In addition, in the reaction formula, X represents the same as the above.)

Synthesis of dicyanotetrahydroquinoxalinedione Compound

A synthesis method for a dicyanotetrahydroquinoxalinedione compound (hereinafter referred to as a "compound (13)") represented by formula (13) below in which a substituent on a nitrogen atom of a piperazinedione ring is hydrogen is described as a synthesis example in European Journal of Organic Chemistry, 4535 (2007).

A compound in which $R^9$ and $R^{10}$ in the general formula (3) are the same other than hydrogen (when $R^9$ and $R^{10}$ are the same other than hydrogen, both are denoted by $R^{11}$, and the compound is represented by general formula (14)) can be synthesized by the following method. The compound (13) is reacted with a compound, such as alkyl halide, aralkyl halide, or the like, in a solvent such as N,N-dimethylformamide, N-methyl-2-pyrrolidinone, dimethylsulfoxide, or the like in the presence of a base such as cesium carbonate, sodium hydride, potassium tert-butoxide, or the like, producing a compound (14) in which $R^9$ and $R^{10}$ in a dicyanotetrahydroquinoxalinedione compound (hereinafter referred to as a "compound (3)") represented by the general formula (3) is the same other than hydrogen.

[Chem. 8]

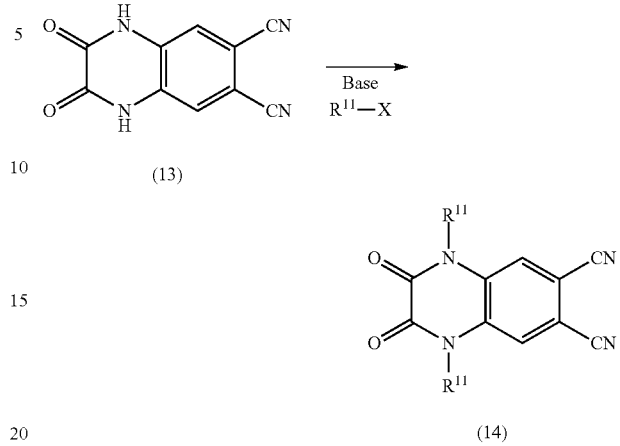

(In the general formula (14), $R^{11}$ represents an alkyl group having 1 to 6 carbon atoms or an aralkyl group having 7 to 9 carbon atoms, and X represents a chlorine atom, a bromine atom, an iodine atom, a tosyl group, a mesyl group, or a sulfonate group such as trifluoromethanesulfonic acid group.)

A compound having $R^9$ and $R^{10}$ which are different in the general formula (3) (when $R^9$ and $R^{10}$ are different, both are denoted by $R^{12}$ and $R^{13}$, and the compound is represented by general formula (20) hereinafter) can be synthesized by, for example, the following method. A compound (16) is produced by substituting, with amine, nitro groups of compound (15) produced by dinitrating the 4- and 5-positions of o-dibromobenzene. Then, the bromine atoms are substituted with amino groups to produce compound (17), and the nitro group is reduced to produce diamino compound (18). According to the above-described method, the compound (18) can be converted to the dicyanotetrahydroquinoxalinedione compound (20) in which $R^9$ and $R^{10}$ the general formula (3) are different from each other. This synthesis method is described in detail in Chemical Communications, 2236 (2002).

[Chem. 9]

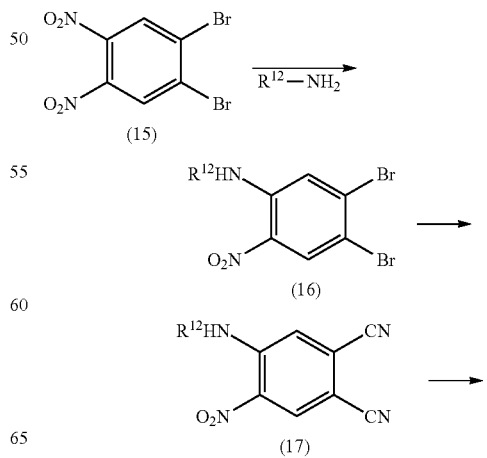

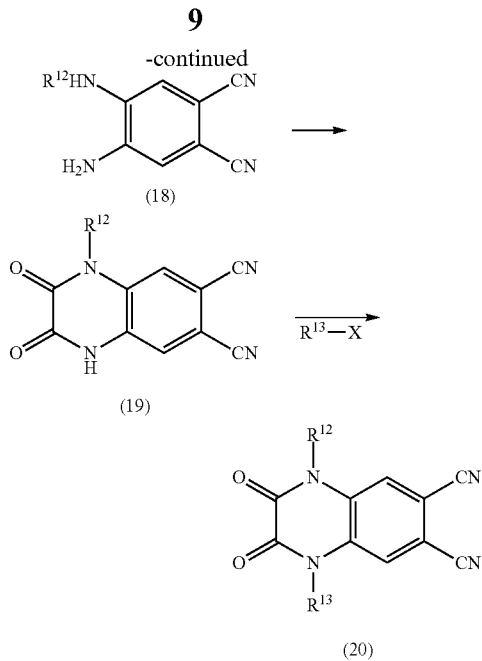

(In the general formula (20), $R^{12}$ and $R^{13}$ each independently represent an alkyl group having 1 to 6 carbon atoms or an aralkyl group having 7 to 9 carbon atoms (excluding a case in which $R^{12}$ and $R^{13}$ are the same). In addition, in the reaction formula, X represents the same as the above.)

Synthesis of Compound (1-1) or Compound (1-2)

The compound (1-1) of the present invention can be produced by thermally condensing, in an organic solvent at 120 to 250° C., the compound (2) or compound (3) produced by the above-described synthesis method with a metal salt corresponding to the divalent to tetravalent metal atom represented by M in the general formula (1-1). In addition, a compound in which $R^1$ to $R^8$ in the general formula (1-1) are different from each other can be produced using two or more types of compounds (2) or compounds (3) each having different $R^9$ and $R^{10}$. A compound in which in the general formula (1-1), n=2 and $R^1$ to $R^8$ are each hydrogen can be synthesized by the same method using the compound (13) as a raw material.

In addition, the compound (1-2) of the present invention can be synthesized by the same synthesis method without using a metal salt corresponding to the divalent to tetravalent metal atom.

Examples of the divalent to tetravalent metal atom represented by M in the general formula (1-1) include magnesium, aluminum, titanium, vanadium, iron, cobalt, nickel, copper, zinc, platinum, palladium, and the like. Among these, titanium, vanadium, iron, cobalt, nickel, copper, and zinc are preferred, and vanadium, cobalt, copper, and zinc are most preferred. These metals may be oxidized.

As the metal salt corresponding to the divalent to tetravalent metal atom, various salts, such as a halogen salt, an acetate, a sulfate, a nitrate, a carbonate, and the like, can be used, but a halogen salt and an acetate are preferred.

Examples of the organic solvent used for synthesizing the compound (1-1) or the compound (1-2) include alcohols, glycols, trichlorobenzene, quinoline, α-chloronaphthalene, nitrobenzene, sulfolane, N,N-dimethylformamide, and the like. The reaction may be effected without using the solvent.

In synthesizing the compound (1-1) or the compound (1-2), an alkali or an organic amine such as 1,8-diazabicyclo[5.4.0]undeca-7-ene (hereinafter, referred to as "DBU"), cyclohexylamine, or the like is preferably used as a catalyst because yield is improved.

Examples of an alkyl group having 1 to 6 carbon atoms and represented by $R^1$ to $R^8$ in the compound (1-1) and the compound (1-2) include a methyl group, an ethyl group, a propyl group, an isopropyl group, a butyl group, a pentyl group, a hexyl group, and the like. Examples of an aralkyl group having 7 to 9 carbon atoms include a benzyl group, a 2-phenylethyl group, a 3-phenylpropyl group, and the like. As the number of carbon atoms in the alkyl group or the aralkyl group increases, durability to the organic solvent tends to decrease.

In particular, as each of $R^1$ to $R^8$ in the general formula (1-1) and the general formula (1-2), a methyl group, an ethyl group, a propyl group, and a butyl group are preferred, and a methyl group, an ethyl group, and a propyl group are particularly preferred.

A compound described in Patent Literature 3 in which in the general formula (1-1) and the general formula (1-2), n=2, and $R^1$ to $R^8$ are hydrogen atoms, and a compound in which in the general formula (1-2) and the general formula (1-2), n=2, and $R^1$ to $R^8$ are hydrogen atoms have low chroma but cause significant aggregation. This is considered to be due to the fact that since the imdazolone ring and the piperazinedione ring have a hydrogen atom on each of the nitrogen atoms, strong intermolecular hydrogen bonding force occurs, thereby increasing aggregation and consequently decreasing chroma. A compound having a substituent other than a hydrogen atom on each of the nitrogen atoms of the imdazolone ring or the piperazinedione ring in the compound (1-1) or the compound (1-2) of this application is considered to cause no aggregation and produce a hue with high chroma.

The compound (1-1) or the compound (1-2) can be produced as a crude green pigment by the above-described synthesis method, but the compound is preferably subjected to pigmentation treatment when being used as a coloring agent. Examples of a method for the pigmentation treatment include grinding such as solvent salt milling, salt milling, dry milling, solvent milling, acid pasting, and the like, and solvent heating. At the same time, the particle diameter of a pigment can also be adjusted by the pigment-forming treatment.

When the phthalocyanine compound of the present invention is used as a green pigment, the compound is preferably used after the particle diameter of the pigment is adjusted in the range of 0.01 to 1 μm by the pigment-forming treatment. The solvent salt milling is preferred as the pigment-forming treatment because it produces the pigment having, in an electron microscope photograph of the resultant pigment, an average length/width ratio (so-called average aspect ratio) of the particles of less than 3 and closer to 1 and a narrower particle size distribution.

A coloring composition of the present invention is a composition containing the phthalocyanine compound of the present invention as a coloring agent together with a synthetic resin. Examples of the composition include a printing ink, a coating material, a colored plastic, a toner, an ink jet for ink, a color paste for a color filter, a color resist, and the like.

Examples of the synthetic resin used for preparing the coloring composition of the present invention include polymerization resins and condensation resins, particularly urea resin/formaldehyde resins, melamine/formaldehyde resins, alkyd resins, phenol resins, polyester resins, polyamide resins, polyvinyl chloride, polyurethane, acryl/melamine, polystyrene, cellulose ester, nitrocellulose, polyacrylate, polyacrylonitrile, polyolefins, and the like. These can be used alone or as a mixture.

The coloring composition of the present invention can be easily prepared by mixing, for example, 100 to 2,000 parts of the synthetic resin (nonvolatile content) relative to 100 parts of the phthalocyanine compound of the present invention according to the purpose of coloring.

In addition, as a filler used for preparing a printing ink, a coating material, a colored plastic, or the like, for example, various metal foils, titanium oxide, silica, and the like can be used. In addition, a surfactant, an antiseptic agent, etc. can be used as various additives, and water and various organic solvents which do not change the crystal state of the pigment can be used as the solvent.

EXAMPLES

The present invention is described in further detail below with reference to examples. Synthesized compounds were analyzed using apparatuses described below unless otherwise specified.

NMR analysis: using nuclear magnetic resonance apparatus "JNM-LA300" manufactured by JEOL, Ltd. and TMS as an internal standard.

Infrared spectroscopic analysis: using infrared spectrophotometer "FT/IR-4200" manufactured by JASCO Corporation or infrared spectrophotometer "SPECTRUM ONE" manufactured by Perkin Elmer Corp.

FD/MS analysis: mass spectrometer "JMS-700" manufactured by JEOL, Ltd.

Ultraviolet-visible spectroscopic analysis: spectrophotometer "U-4100" manufactured by Hitachi, Ltd.

Synthesis Example 1

Synthesis of Compound (5)

First, 39.0 parts by mass of 1,2-diamino-4,5-dicyanobenzene and 50.8 parts by mass of 1,1'-carbonylbis-1H-imidazole were added to 245 parts by mass of dehydrated acetonitrile, followed by stirring at 70° C. for 4 hours. Then, the resultant reaction mixture was cooled to room temperature, and the precipitated solid was filtered off, washed with acetonitrile, and dried under reduced pressure to produce 43.5 parts by mass (yield 96%) of the target compound.

With respect to the resultant compound, $^1$H- and $^{13}$C-NMR analysis in a dimethylsulfoxide (hereinafter referred to as "DMSO")-$d_6$ solution and infrared spectroscopic analysis by a KBr disk method were conducted to obtain analytical results described below.

<NMR Analysis>
$^1$H-NMR (DMSO-$d_6$) δ 7.61 (s, 2H), 11.7 (br, 2H)
$^{13}$C-NMR (DMSO-$d_6$): δ 105.7, 111.9, 115.7, 132.2, 153.9
<Infrared Spectroscopic Analysis>
3314 (N—H stretching vibration), 2241 (cyano group CN stretching vibration), 1728 (C=O stretching vibration) cm$^{-1}$ It was confirmed from the above results that the compound produced in Synthesis Example 1 is a dicyanobenzimidazolone compound represented by the formula (5).

Synthesis Example 2

Synthesis of dicyanobenzimidazolone Compound Having methyl Groups as $R^9$ and $R^{10}$ in the General Formula (2)

First, 3.91 parts by mass of sodium hydride (60% dispersion in paraffin) was added to 95 parts by mass of dehydrated N,N-dimethylformamide, and 9.0 parts by mass of the compound (5) was added to the resultant mixture while the inner temperature was maintained at 25 to 30° ° C. by cooling with ice. Then, 14.6 parts by mass of methyl iodide was added dropwise to the mixture, followed by further stirring at room temperature for 1 hour. The reaction mixture was poured into 300 parts by mass of ice water, and the precipitated solid was filtered off, washed with water and n-hexane, and then dried under reduced pressure to produce 8.45 parts by mass (yield 82%) of the target compound.

With respect to the compound produced in Synthesis Example 2, $^1$H- and $^{13}$C-NMR analysis in a DMSO-$d_6$ solution and infrared spectroscopic analysis by a KBr disk method were conducted to obtain analytical results described below.

<NMR Analysis>
$^1$H-NMR (DMSO-d): δ 3.40 (s, 6H), 8.00 (s, 2H)
$^{13}$C-NMR (DMSO-$d_6$): δ 27.6, 106.7, 112.6, 116.8, 133.0, 153.9
<Infrared Spectroscopic Analysis>
2955 (methyl group C—H stretching vibration), 2226 (cyano group CN stretching vibration), 1728 (C=O stretching vibration) cm$^{-1}$ It was confirmed from the above analytical results that the compound produced in Synthesis Example 2 is a N,N'-disubstituted dicyanobenzimidazolone compound represented by formula (21) below.

[Chem. 10]

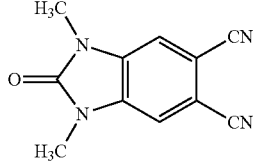

(21)

Synthesis Example 3

Synthesis of dicyanobenzimidazolone Compound Having ethyl Groups as $R^9$ and $R^{10}$ in the General Formula (2)

First, 5.70 parts by mass of sodium hydride (60% dispersion in paraffin) was added to 115 parts by mass of dehydrated N,N-dimethylformamide, and 12.8 parts by mass of the compound (5) was added to the resultant mixture while the inner temperature was maintained at 20 to 35° C. by cooling with ice. Then, 22.2 parts by mass of ethyl iodide dissolved in 19 parts by mass of dehydrated N,N-dimethylformamide was added dropwise to the mixture, followed by further stirring at room temperature for 4 hours. The reaction mixture was poured into 400 parts by mass of ice water, and the precipitated solid was filtered off, washed with water and n-hexane, and then dried under reduced pressure to produce 14.2 parts by mass (yield 85%) of the target compound.

With respect to the compound produced in Synthesis Example 3, $^1$H- and $^{13}$C-NMR analysis in a DMSO-$d_6$ solution and infrared spectroscopic analysis by a Br disk method were conducted to obtain analytical results described below.
<NMR Analysis>
$^1$H-NMR (DMSO-$d_6$): δ 1.21 (t, j=7.1 Hz, 6H), 3.93 (q, j=7.1 Hz, 4H), 8.07 (s, 2H)

$^{13}$C-NMR (DMSO-d$_6$): δ 13.3, 36.1, 106.8, 112.7, 116.8, 132.0, 152.9

<Infrared Spectroscopic Analysis>

2924 (ethyl group C—H stretching vibration), 2228 (cyano group CN stretching vibration), 1716 (C=O stretching vibration) cm$^{-1}$ It was confirmed from the above analytical results that the compound produced in Synthesis Example 3 is a N,N'-disubstituted dicyanobenzimidazolone compound represented by formula (22) below.

[Chem. 11]

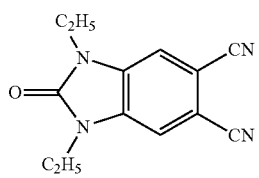

(22)

Synthesis Example 4

Synthesis of dicyanobenzimidazolone Compound Having propyl Groups as R$^9$ and R$^{10}$ in the General Formula (2)

First, 1.78 parts by mass of sodium hydride (60% dispersion in paraffin) was added to 38 parts by mass of dehydrated N,N-dimethylformamide, and 4.0 parts by mass of the compound (5) was added to the resultant mixture while the inner temperature was maintained at 20 to 35° C. by cooling with ice. Then, 7.57 parts by mass of propyl iodide dissolved in 9 parts by mass of dehydrated N,N-dimethylformamide was added dropwise to the mixture, followed by further stirring at room temperature for 5 hours. The reaction mixture was poured into 200 parts by mass of ice water, and the precipitated solid was filtered off, washed with water and n-hexane, and then dried under reduced pressure to produce 4.43 parts by mass (yield 76%) of the target compound.

With respect to the compound produced in Synthesis Example 4, $^1$H- and $^{13}$C-NMR analysis in a DMSO-d$_6$ solution and infrared spectroscopic analysis by a KBr disk method were conducted to obtain analytical results described below.

<NMR Analysis>

$^1$H-NMR (DMSO-d$_6$): δ 0.86 (t, j=7.4 Hz, 6H), 1.67 (m, 4H), 3.87 (t, j=7.2 Hz, 4H), 8.11 (s, 2H)

$^{13}$C-NMR (DMSO-d$_6$): δ 10.8, 21.0, 42.5, 106.8, 112.8, 116.8, 132.4, 153.5

<Infrared Spectroscopic Analysis>

2964 (propyl group C—H stretching vibration), 2224 (cyano group CN stretching vibration), 1710 (C=O stretching vibration) cm$^{-1}$ It was confirmed from the above analytical results that the compound produced in Synthesis Example 4 is a N,N'-disubstituted dicyanobenzimidazolone compound represented by formula (23) below.

[Chem. 12]

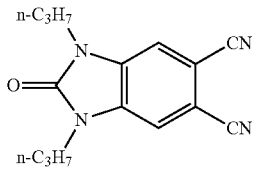

(23)

Synthesis Example 5

Synthesis of dicyanotetrahydroquinoxalinedione Compound Having methyl Groups as R$^9$ and R$^{10}$ in the General Formula (3)

First, 5.00 parts by mass of the compound (13) and 19.2 parts by mass of cesium carbonate were added to 120 parts by mass of dehydrated N,N-dimethylformamide, followed by stirring. Then, 8.36 parts by mass of methyl iodide was added to the resultant mixture at room temperature, followed by further stirring at room temperature overnight. Then, 270 parts by mass of ethyl acetate was added to the reaction mixture, and the precipitated solid was filtered off. Next, 600 parts by mass of water was added to the filtrate, and an organic layer was separated, dried with anhydrous sodium sulfate, and then concentrated. The concentrated residue was added to the first resulting solid, and the mixture was recrystallized with a mixed solvent of acetone, ethyl acetate, and hexane (mass ratio of 10:10:40) to produce 4.02 parts by mass (yield 71%) of the target compound.

With respect to the compound produced in Synthesis Example 5, $^1$H- and $^{13}$C-NMR analysis in a dimethylsulfoxide (hereinafter referred to as "DMSO")-d$_6$ solution and infrared spectroscopic analysis by a KBr disk method were conducted to obtain analytical results described below.

NMR Analysis>

$^1$H-NMR (DMSO-d$_6$): δ 3.55 (s, 6H), 8.17 (s, 2H)

$^{13}$C-NMR (DMSO-d$_6$): δ 30.3, 108.8, 115.8, 120.2, 131.4, 153.5

<Infrared Spectroscopic Analysis>

2960 (methyl group C—H stretching vibration), 2234 (cyano group CN stretching vibration), 1.695 (C=O stretching vibration) cm$^{-1}$ It was confirmed from the above analytical results that the compound produced in Synthesis Example 5 is a dicyanotetrahydroquinoxalinedione compound represented by formula (24) below.

[Chem. 13]

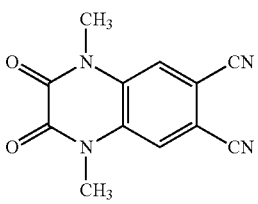

(24)

Synthesis Example 6

Synthesis of dicyanotetrahydroquinoxalinedione Compound Having ethyl Groups as $R^9$ and $R^{10}$ in the General Formula (2)

First, 1.54 parts by mass of sodium hydride (60% dispersion in paraffin) was added to 90 parts by mass of dehydrated N,N-dimethylformamide, followed by stirring at room temperature. Then, 3.71 parts by mass of the compound (13) and 6.55 parts by mass of ethyl iodide were added in order to the resultant mixture, followed by stirring at room temperature overnight. Then, the reaction mixture was poured into 800 parts by mass of water, and the precipitated solid was filtered off. Next, the resultant crude product was suspended in a mixed solvent of acetone, ethyl acetate, and hexane (mass ratio of 10:10:40) and then heated under reflux. After cooling to room temperature, the solid was filtered off to produce 1.69 parts by mass (yield 36%) of the target compound.

With respect to the compound produced in Synthesis Example 6, $^1$H- and $^{13}$C-NMR analysis in a DMSO-$d_6$ solution and infrared spectroscopic analysis by a KBr disk method were conducted to obtain analytical results described below.

<NMR Analysis>
$^1$H-NMR (DMSO-$d_6$): δ 1.19 (t, J=7.0 Hz, 6H), 4.17 (q, J=7.0 Hz, 4H), 8.21 (s, 2H)
$^{13}$C-NMR (DMSO-$d_6$): δ 11.7, 38.1, 109.0, 115.9, 120.2, 130.6, 153.2

<Infrared Spectroscopic Analysis>
2975 (ethyl group C—H stretching vibration), 2232 (cyano group CN stretching vibration), 1709 (C=O stretching vibration) cm$^{-1}$ It was confirmed from the above analytical results that the compound produced in Synthesis Example 6 is a dicyanotetrahydroquinoxalinedione compound represented by formula (25) below.

[Chem. 14]

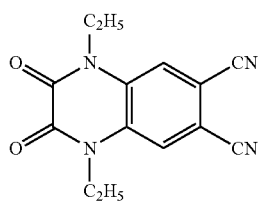

(25)

Syntheses Example 7

Synthesis of dicyanotetrahydroquinoxalinedione Compound Having 1-propyl Groups as $R^9$ and $R^{10}$ in the General Formula (3)

First, 4.45 parts by mass of the compound (13) and 17.1 parts by mass of cesium carbonate were added to 95 parts by mass of dehydrated N,N-dimethylformamide, followed by stirring. Then, 8.93 parts by mass of 1-propyl iodide was added to the resultant mixture at room temperature, followed by stirring at 35° C. for 3 days. Then, the reaction mixture was poured into 400 parts by mass of water, and the precipitated solid was filtered off. Next, the resultant crude product was suspended in 60 parts by mass of ethyl acetate and then heated under reflux. Then, 45 parts by mass of hexane was added, and the precipitated solid was filtered off to produce 2.64 parts by mass (yield 42%) of the target compound.

With respect to the compound produced in Synthesis Example 7, $^1$H- and $^{13}$C-NMR analysis in a DMSO-$d_6$ solution and infrared spectroscopic analysis by a Br disk method were conducted to obtain analytical results described below.

<NMR Analysis>
$^1$H-NMR (DMSO-$d_6$): δ 0.95 (t, J=7.3 Hz, 6H), 1.61 (m, 4H), 4.08 (t, J=7.7 Hz, 4H), 8.23 (s, 2H)
$^{13}$C-NMR (DMSO-$d_6$) δ 10.9, 19.5, 44.3, 108.9, 115.9, 120.3, 130.7, 153.3

<Infrared Spectroscopic Analysis>
2967 (propyl group C—H stretching vibration), 2231 (cyano group CN stretching vibration), 1709 (C=O stretching vibration) cm$^{-1}$ It was confirmed from the above analytical results that the compound produced in Synthesis Example 7 is a dicyanotetrahydroquinoxalinedione compound represented by formula (26) below.

[Chem. 15]

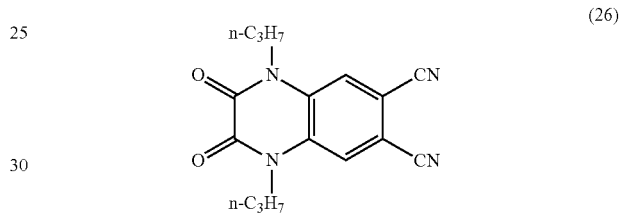

(26)

Example 1

Synthesis of phthalocyanine Compound Having zinc atom as M and methyl Groups as all of $R^1$ to $R^8$ in the General Formula (1-1) (n=1)

First, 2.0 parts by mass of the dicyanobenzimidazolone compound (21) produced in Synthesis Example 2, 0.432 parts by mass of zinc acetate, and 1.45 parts by mass of DBU were added to 20 parts by mass of 1-pentanol, and the resultant mixture was heated under reflux for 6.5 hours while being stirred. The reaction solution was cooled to 70° C. or less, and then the precipitated solid was filtered off. The resultant crude product was washed in order with hot methanol, hot acetone, 1 mol/l hydrochloric acid, 8% by mass ammonia water, hot N,N-dimethylformamide, and methanol to produce, as a green solid, 1.89 parts by mass (yield 88%) of the target phthalocyanine compound.

With respect to the compound produced as described above, FD/MS analysis, infrared spectroscopic analysis by a KBr disk method, and ultraviolet-visible spectroscopic analysis in a sulfuric acid solution were conducted to obtain analytical results described below.

<FD/MS Analysis>
912 M$^+$

<Infrared Spectroscopic Analysis>
2942 (methyl group C—H stretching vibration), 1695 (C=O stretching vibration), 1494, 1081, 745, 5835 cm$^{-1}$ <Ultraviolet-Visible Spectroscopic Analysis>
316, 459, 722, 817 nm It was confirmed from the above results that the green solid produced in Example 1 is zinc tetrabenzimidazolonoporphyrazine represented by formula (27) below.

[Chem. 16]

(27)

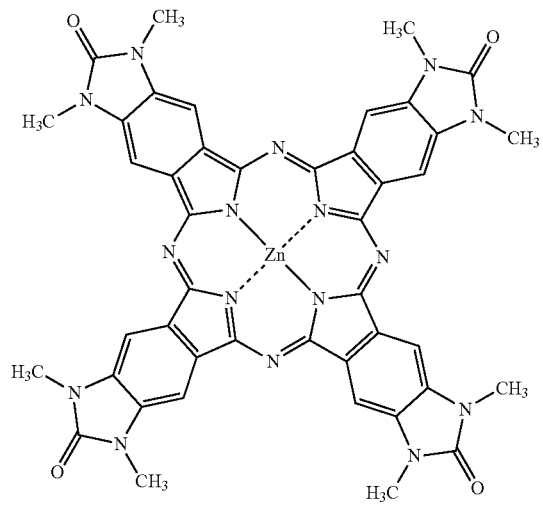

Example 2

Synthesis of phthalocyanine Compound Having copper atom as M and methyl Groups as all of $R^1$ to $R^8$ in the General Formula (1-1) (n=1)

First, 4.71 parts by mass of the dicyanobenzimidazolone compound (21) produced in Synthesis Example 2, 0.633 parts by mass of copper(I) chloride, and 3.90 parts by mass of DBU were added to 45 parts by mass of 1-pentanol, and the resultant mixture was heated under reflux for 9 hours while being stirred. The reaction solution was cooled to 70° C. or less, and then the precipitated solid was filtered off. The resultant crude product was washed in order with hot methanol, hot acetone, 1 mol/l hydrochloric acid, 8% by mass ammonia water, hot N,N-dimethylformamide, and methanol to produce, as a green solid, 4.52 parts by mass (yield 89%) of the target phthalocyanine compound.

With respect to the compound produced as described above, FD/MS analysis, infrared spectroscopic analysis by a KBr disk method, and ultraviolet-visible spectroscopic analysis in a sulfuric acid solution were conducted to obtain analytical results described below.

<FD/MS Analysis>

911 M+

<Infrared Spectroscopic Analysis>

1704 (C=O stretching vibration), 1493, 1439, 1083, 745, 583 cm$^{-1}$

<Ultraviolet-Visible Spectroscopic Analysis>

463, 728, 825 nm

It was confirmed from the above results that the green solid produced in Example 2 is copper tetrabenzimidazolonoporphyrazine represented by formula (28) below.

[Chem. 17]

(28)

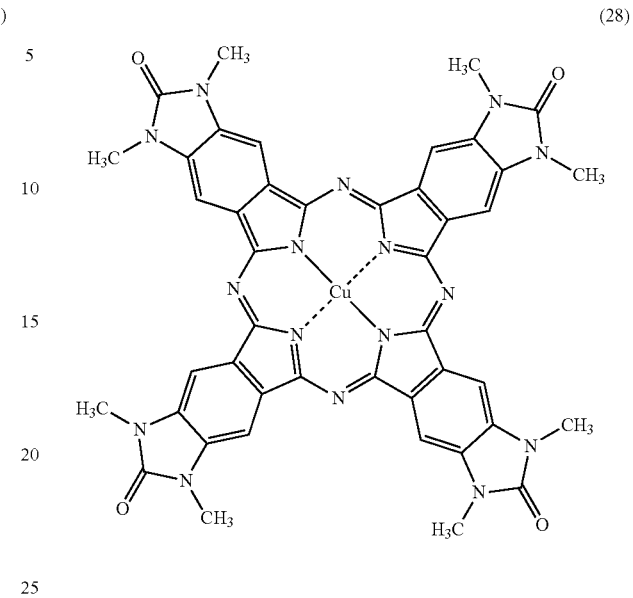

Example 3

Synthesis of phthalocyanine Compound Having zinc atom as M and ethyl Groups as all of $R^1$ to $R^8$ the General Formula (1-1) (n=1)

First, 8.67 parts by mass of the dicyanobenzimidazolone compound (22) produced in Synthesis Example 3, 1.66 parts by mass of zinc acetate, and 5.49 parts by mass of DBU were added to 82 parts by mass of 1-pentanol, and the resultant mixture was heated under reflux for 7 hours while being stirred. The reaction solution was cooled to 70° C. or less, and then the precipitated solid was filtered off. The resultant crude product was washed in order with hot methanol, hot acetone, 1 mol/l hydrochloric acid, 8% by mass ammonia water, hot N,N-dimethylformamide, and methanol to produce, as a green solid, 5.42 parts by mass (yield 59%) of the target phthalocyanine compound.

With respect to the compound produced as described above, FD/MS analysis, infrared spectroscopic analysis by a KBr disk method, and ultraviolet-visible spectroscopic analysis in a N-methyl-2-pyrrolidinone solution were conducted to obtain analytical results described below.

<FD/MS Analysis>

1024 M+

<Infrared Spectroscopic Analysis>

2973 (ethyl group C—H stretching vibration), 1693 (C=O stretching vibration), 1487, 1417, 1080, 731, 586 cm$^{-1}$ <Ultraviolet-Visible Spectroscopic Analysis>

307, 363, 622, 691 nm

It was confirmed from the above results that the green solid produced in Example 3 is zinc tetrabenzimidazolonoporphyrazine represented by formula (29) below.

[Chem. 18]

(29)

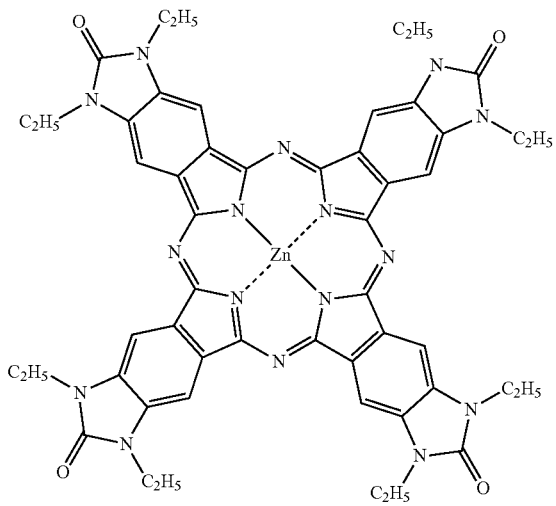

Example 4

Synthesis of phthalocyanine Compound Having copper atom as M and ethyl Groups as all of $R^1$ to $R^8$ in the General Formula (1-1) (n=1)

First, 2.40 parts by mass of the dicyanobenzimidazolone compound (22) produced in Synthesis Example 3, 0.250 parts by mass of copper(I) chloride, and 1.52 parts by mass of DBU were added to 20 parts by mass of 1-pentanol, and the resultant mixture was heated under reflux for 7 hours while being stirred. The reaction solution was cooled to 70° C. or less, and then the precipitated solid was filtered off. The resultant crude product was washed in order with hot methanol, hot acetone, 1 mol/l hydrochloric acid, 8% by mass ammonia water, hot N,N-dimethylformamide, and methanol to produce, as a green solid, 1.96 parts by mass (yield 76%) of the target phthalocyanine compound.

With respect to the compound produced as described above, FD/MS analysis, infrared spectroscopic analysis by a KBr disk method, and ultraviolet-visible spectroscopic analysis in a sulfuric acid solution were conducted to obtain analytical results described below.

<FD/MS Analysis>

1023 M+

<Infrared Spectroscopic Analysis>

2969 (ethyl group C—H stretching vibration), 1710 (C=O stretching vibration), 1490, 1428, 1083, 746, 588 cm$^{-1}$ <Ultraviolet-Visible Spectroscopic Analysis>

467, 730, 829 nm

It was confirmed from the above results that the green solid produced in Example 4 is copper tetrabenzimidazolonoporphyrazine represented by formula (30) below.

[Chem. 19]

(30)

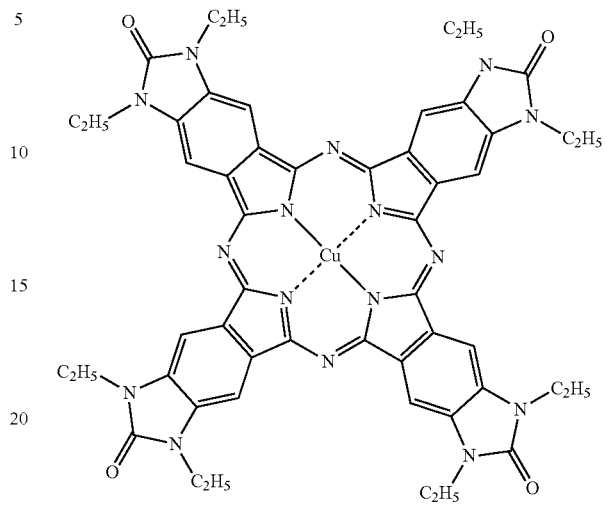

Example 5

Synthesis of phthalocyanine Compound Having cobalt atom as M and ethyl Groups as all of $R^1$ to $R^8$ in the General Formula (1-1) (n=1)

First, 3.00 parts by mass of the dicyanobenzimidazolone compound (22) produced in Synthesis Example 3, 0.683 parts by mass of cobalt(II) bromide, and 1.90 parts by mass of DBU were added to 30 parts by mass of 1-pentanol, and the resultant mixture was heated under reflux for 8 hours while being stirred. The reaction solution was cooled to 70° C. or less, and then the precipitated solid was filtered off. The resultant crude product was washed in order with hot methanol, hot acetone, 1 mol/l hydrochloric acid, 8% by mass ammonia water, hot N,N-dimethylformamide, and methanol to produce, as a dark green solid, 1.41 parts by mass (yield 44%) of the target phthalocyanine compound.

With respect to the compound produced as described above, FD/MS analysis, infrared spectroscopic analysis by a KBr disk method, and ultraviolet-visible spectroscopic analysis in a N-methyl-2-pyrrolidinone solution were conducted to obtain analytical results described below.

<FD/MS Analysis>

1019 M+

<Infrared spectroscopic Analysis>

2978 (ethyl group C—H stretching vibration), 1706 (C=O stretching vibration), 1490, 1434, 1082, 749, 587 cm$^{-1}$ <Ultraviolet-Visible Spectroscopic Analysis>

379, 620, 691 nm

It was confirmed from the above results that the dark green solid produced in Example 5 is cobalt tetrabenzimidazolonoporphyrazine represented by formula (31) below.

[Chem. 20]

(31)

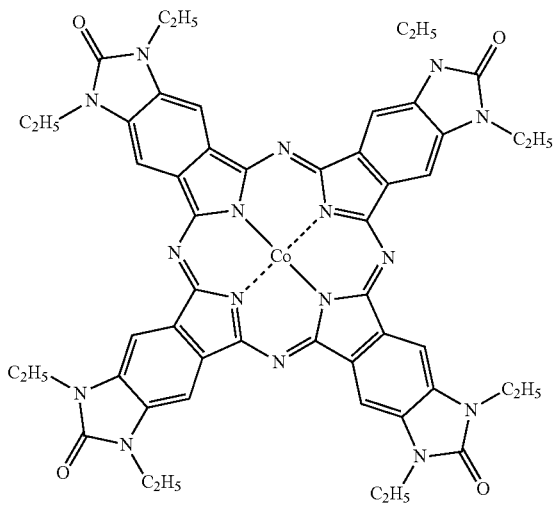

Example 6

Synthesis of phthalocyanine Compound Having V=O as N and ethyl Groups as all of $R^1$ to $R^8$ in the General Formula (1-1) (n=1)

First, 2.00 parts by mass of the dicyanobenzimidazolone compound (22) produced in Synthesis Example 3, 0.344 parts by mass of vanadium(III) chloride, and 1.27 parts by mass of DBU were added to 25 parts by mass of 1-pentanol, and the resultant mixture was heated under reflux for 9 hours while being stirred. The reaction solution was cooled to 70° C. or less, and then the precipitated solid was filtered off. The resultant crude product was washed in order with hot methanol, hot acetone, 1 mol/l hydrochloric acid, 8% by mass ammonia water, hot N,N-dimethylformamide, and methanol to produce, as a green solid, 0.823 parts by mass (yield 39%) of the target phthalocyanine compound.

With respect to the compound produced as described above, FD/MS analysis, infrared spectroscopic analysis by a KBr disk method, and ultraviolet-visible spectroscopic analysis in a N-methyl-2-pyrrolidinone solution were conducted to obtain analytical results described below.

<FD/MS Analysis>
1027 M$^+$
<Infrared Spectroscopic Analysis>
2978 (ethyl group C—H stretching vibration), 1709 (C=O stretching vibration), 1493, 1427, 1081, 754, 587 cm$^{-1}$
<Ultraviolet-Visible Spectroscopic Analysis>
315, 344, 444, 649, 723 nm It was confirmed from the above results that the green solid produced in Example 6 is vanadium oxide tetrabenzimidazolonoporphyrazine represented by formula (32) below.

[Chem. 21]

(32)

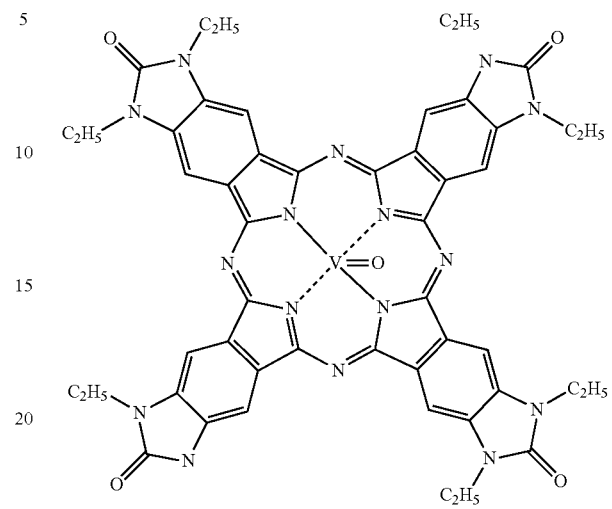

Example 7

Synthesis of phthalocyanine Compound Having zinc atom as M and propyl Groups as all of $R^1$ to $R^8$ in the General Formula (1-1) (n=1)

First, 2.00 parts by mass of the dicyanobenzimidazolone compound (23) produced in Synthesis Example 4, 0.349 parts by mass of zinc acetate, and 1.13 parts by mass of DBU were added to 20 parts by mass of 1-pentanol, and the resultant mixture was heated under reflux for 9 hours while being stirred. The reaction solution was cooled to 70° C. or less, and then the precipitated solid was filtered off. The resultant crude product was washed in order with hot methanol, hot acetone, 1 mol/l hydrochloric acid, 8% by mass ammonia water, hot N,N-dimethyl formamide, and methanol to produce, as a green solid, 1.20 parts by mass (yield 57%) of the target phthalocyanine compound.

With respect to the compound produced as described above, FD/MS analysis, infrared spectroscopic analysis by a KBr disk method, and ultraviolet-visible spectroscopic analysis in a N-methyl-2-pyrrolidinone solution were conducted to obtain analytical results described below.

<FD/MS Analysis>
1136 M$^+$
<Infrared Spectroscopic Analysis>
2967 (propyl group C—H stretching vibration), 1714 (C=O stretching vibration), 1488, 1419, 1090, 748 cm$^{-1}$
<Ultraviolet-Visible Spectroscopic Analysis>
306, 363, 623, 692 nm It was confirmed from the above results that the green solid produced in Example 7 is zinc tetrabenzimidazolonoporphyrazine represented by formula (33) below.

[Chem. 22]

(33)

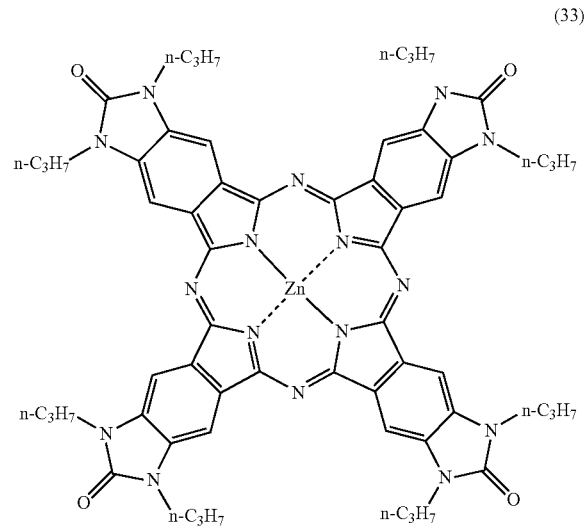

Example 8

Synthesis of phthalocyanine Compound Having methyl Groups as all of $R^1$ to $R^8$ in the General Formula (1-2) (n=1)

First, 1.00 parts by mass of the dicyanobenzimidazolone compound (21) produced in Synthesis Example 2 and 0.72 parts by mass of DBU were added to 8.15 parts by mass of 1-pentanol, and the resultant mixture was heated under reflux for 24 hours while being stirred. The reaction solution was cooled to 70° C. or less, and then the precipitated solid was filtered off. The resultant crude product was washed in order with hot methanol, hot acetone, 1 mol/l hydrochloric acid, 8% by mass ammonia water, hot N,N-dimethylformamide, and methanol to produce, as a green solid, 0.13 parts by mass (yield 13%) of the target phthalocyanine compound.

With respect to the compound produced as described above, FD/MS analysis, infrared spectroscopic analysis by a KBr disk method, and ultraviolet-visible spectroscopic analysis in a sulfuric acid solution were conducted to obtain analytical results described below.

<FD/MS Analysis>
850 M$^+$

<Infrared Spectroscopic Analysis>
1705 (C═O stretching vibration), 1494, 1080, 1024, 742, 582 cm$^{-1}$ <Ultraviolet-Visible Spectroscopic Analysis>
312, 459, 781, 825, 871 nm It was confirmed from the above results that the green solid produced in Example 8 is metal-free tetrabenzimidazolonoporphyrazine represented by formula (34) below.

[Chem. 23]

(34)

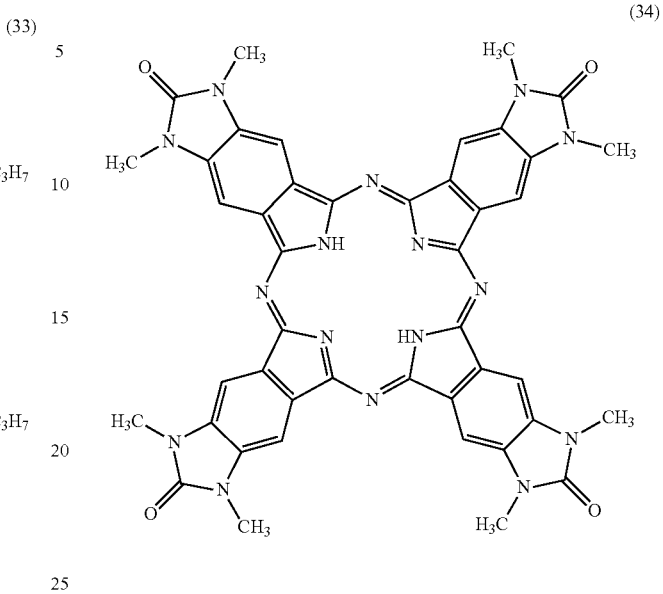

Example 9

Synthesis of phthalocyanine Compound Having ethyl Groups as all of $R^1$ to $R^8$ in the General Formula (1-2) (n=1)

First, 10.0 parts by mass of the dicyanobenzimidazolone compound (22) produced in Synthesis Example 3 and 6.34 parts by mass of DBU were added to 82 parts by mass of 1-pentanol, and the resultant mixture was heated under reflux for 9 hours while being stirred. The reaction solution was cooled to 70° C. or less, and then the precipitated solid was filtered off. The resultant crude product was washed in order with hot methanol, hot acetone, 1 mol/l hydrochloric acid, 8% by mass ammonia water, hot N,N-dimethylformamide, and methanol to produce, as a green solid, 5.53 parts by mass (yield 551) of the target phthalocyanine compound.

With respect to the compound produced as described above, FD/MS analysis, infrared spectroscopic analysis by a KBr disk method, and ultraviolet-visible spectroscopic analysis in a sulfuric acid solution were conducted to obtain analytical results described below.

<FD/MS Analysis>
962 M$^+$

<Infrared Spectroscopic Analysis>
2978 (ethyl group C—H stretching vibration), 1710 (C═O stretching vibration), 1492, 1473, 1077, 1027, 749, 587 cm$^{-1}$ <Ultraviolet-Visible Spectroscopic Analysis>
313, 465, 785, 827, 876 nm It was confirmed from the above results that the green solid produced in Example 9 is metal-free tetrabenzimidazolonoporphyrazine represented by formula (35) below.

[Chem. 24]

(35)

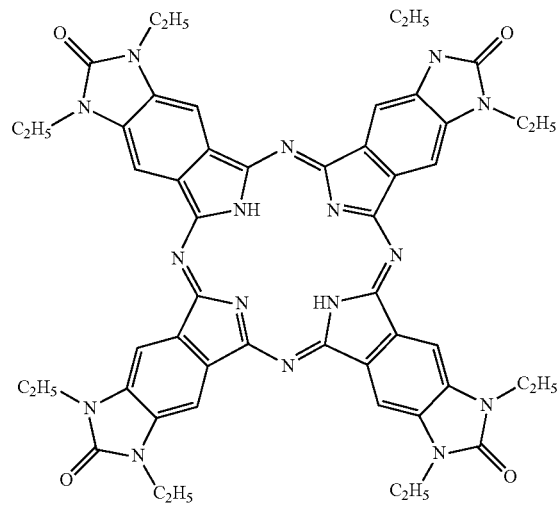

Example 10

Synthesis of phthalocyanine Compound Having zinc atom as M and methyl Groups as all of $R^1$ to $R^8$ in the General Formula (1-1) (n=2)

First, 2.40 parts by mass of the dicyanotetrahydroquinoxaliinedione compound (24) produced in Synthesis Example 5, 0.46 parts by mass of zinc acetate, and 1.52 parts by mass of DBU were added to 25 parts by mass of 1-pentanol, and the resultant mixture was heated under reflux for 7 hours while being stirred. The reaction solution was cooled to 70° C. or less, and then the precipitated solid was filtered off. The resultant crude product was washed in order with hot methanol, hot acetone, 1 mol/l hydrochloric acid, 8% by mass ammonia water, water, hot N,N-dimethylformamide, and methanol to produce, as a green solid, 1.74 parts by mass (yield 68%) of the target phthalocyanine compound.

With respect to the green solid produced as described above, FD/MS analysis, infrared spectroscopic analysis by a KBr disk method, and ultraviolet-visible spectroscopic analysis in a N,N-dimethylformamide solution were conducted to obtain analytical results described below.

<Ft/MS Analysis> m/z=1024 M$^+$

<Infrared Spectroscopic Analysis>

1678 (C=O stretching vibration), 1461, 1383, 1104, 744 cm$^{-1}$

<Ultraviolet-Visible Spectroscopic Analysis>

Absorption wavelength: 313, 375, 693 nm

It was confirmed from the above results that the green solid produced in Example 10 is a zinc tetra(tetrahydroquinoxalinediono)porphyrazine compound represented by formula (36) below.

[Chem. 25]

(36)

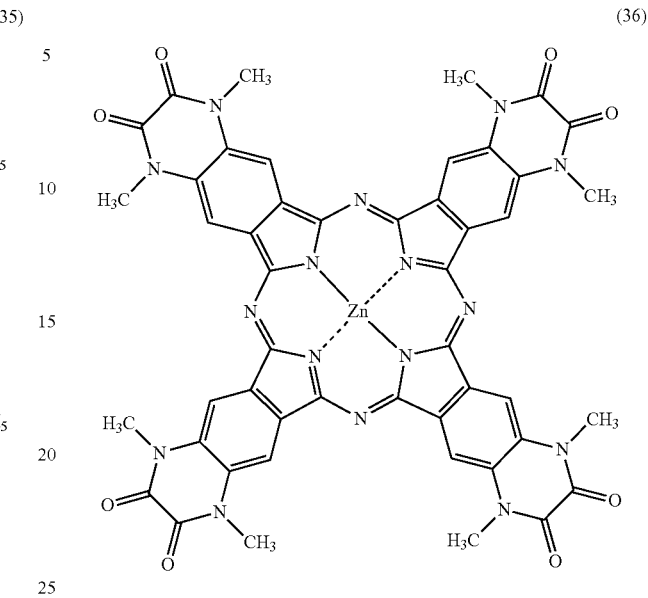

Example 11

Synthesis of phthalocyanine Compound Having copper atom as M and methyl Groups as all of $R^1$ to $R^8$ in the General Formula (1-1) (n=2)

First, 0.10 parts by mass of the dicyanotetrahydroquinoxalinedione compound (24) produced in Synthesis Example 5, 0.0107 parts by mass of copper(I) chloride, and 0.0761 parts by mass of DBU were added to 4 parts by mass of 1-pentanol, and the resultant mixture was heated under reflux for 4.5 hours while being stirred. The reaction solution was cooled to 70° C. or less, and then the precipitated solid was filtered off. The resultant crude product was washed in order with hot acetone, 1 mol/l hydrochloric acid, 8% by mass ammonia water, water, hot N,N-dimethylformamide, and acetone to produce, as a green solid, 0.0932 parts by mass (yield 87%) of the target phthalocyanine compound.

With respect to the green solid produced as described above, FD/MS analysis, infrared spectroscopic analysis by a KBr disk method, and ultraviolet-visible spectroscopic analysis in a sulfuric acid solution were conducted to obtain analytical results described below.

<FD/MS Analysis> m/z=1023 M$^+$

<Infrared Spectroscopic Analysis>

1679 (C=O stretching vibration), 1464, 1387, 1113, 745 cm$^{-1}$

<Ultraviolet-Visible Spectroscopic Analysis>

Absorption wavelength: 326, 769, 798 nm

It was confirmed from the above results that the green solid produced in Example 11 is a copper tetra(tetrahydroquinoxalinediono)porphyrazine compound represented by formula (37) below.

[Chem. 26]

(37)

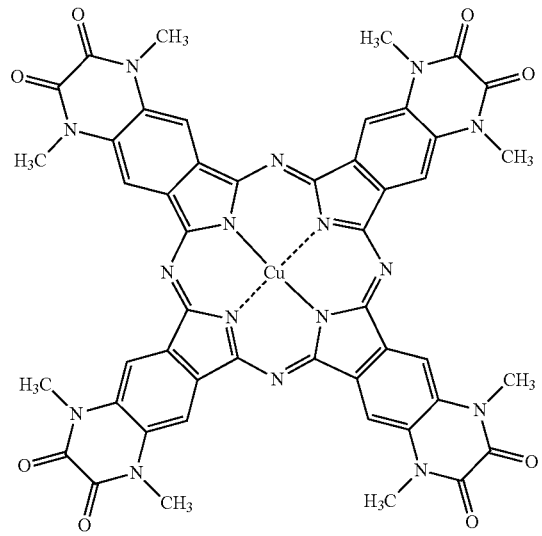

Example 12

Synthesis of phthalocyanine Compound Having zinc atom as M and ethyl Groups as all of $R^1$ to $R^8$ in the General Formula (1-1) (n=2)

First, 1.67 parts by mass of the dicyanotetrahydroquinoxalinedione compound (25) produced in Synthesis Example 6, 0.29 parts by mass of zinc acetate, and 0.95 parts by mass of DBU were added to 20 parts by mass of 1-pentanol, and the resultant mixture was heated under reflux for 6 hours while being stirred. The reaction solution was cooled to 70° C. or less, and then the precipitated solid was filtered off. The resultant crude product was washed in order with hot methanol, hot acetone, 1 mol/l hydrochloric acid, 8% by mass ammonia water, water, hot N,N-dimethylformamide, and methanol to produce, as a green solid, 0.61 parts by mass (yield 34%) of the target phthalocyanine compound.

With respect to the green solid produced as described above, FD/MS analysis, infrared spectroscopic analysis by a KBr disk method, and ultraviolet-visible spectroscopic analysis in a N-methyl-2-pyrrolidinone solution were conducted to obtain analytical results described below.

<FD/MS Analysis> m/z=1136 $M^+$

<Infrared Spectroscopic Analysis>

2981 (ethyl group C—H stretching vibration), 1667 (C=O stretching vibration), 1469, 1401, 1107, 744 $cm^{-1}$ <Ultraviolet-Visible Spectroscopic Analysis>

Absorption wavelength: 317, 366, 698 nm

It was confirmed from the above results that the green solid produced in Example 12 is a zinc tetra(tetrahydroquinoxalinediono)porphyrazine compound represented by formula (38) below.

[Chem. 27]

(38)

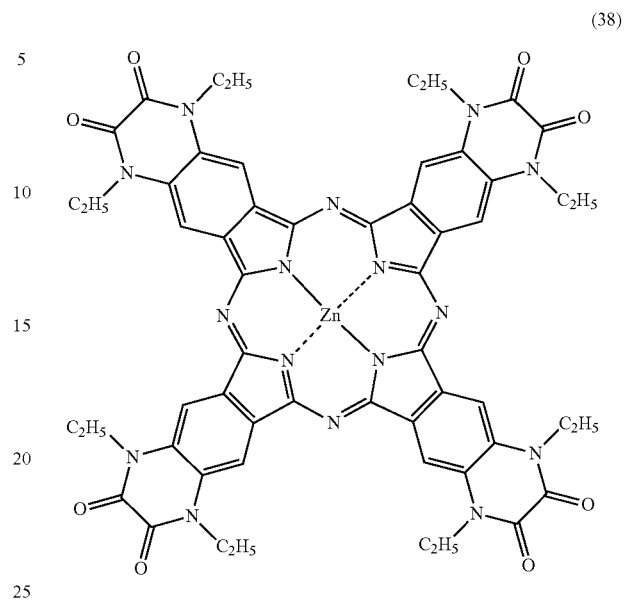

Example 13

Synthesis of phthalocyanine Compound Having zinc atom as M and propyl Groups as all of $R^1$ to $R^8$ in the General Formula (1-1) (n=2)

First, 2.64 parts by mass of the dicyanotetrahydroquinoxalinedione compound (26) produced in Synthesis Example 7, 0.42 parts by mass of zinc acetate, and 1.36 parts by mass of DBU were added to 25 parts by mass of 1-pentanol, and the resultant mixture was heated under reflux for 8.5 hours while being stirred. The reaction solution was cooled to 70° C. or leas, and then the precipitated solid was filtered off. The resultant crude product was washed in order with hot methanol, hot acetone, 1 mol/l hydrochloric acid, 8% by mass ammonia water, water, hot N,N-dimethylformamide, and methanol to produce, as a green solid, 1.34 parts by mass (yield 48%) of the target phthalocyanine compound.

With respect to the green solid produced as described above, FD/MS analysis, infrared spectroscopic analysis by a KBr disk method, and ultraviolet-visible spectroscopic analysis in a N-methyl-2-pyrrolidinone solution were conducted to obtain analytical results described below.

<FD/MS Analysis> m/z=1248 $M^+$

<Infrared Spectroscopic Analysis>

2963 (propyl group C—H stretching vibration), 1677 (C=O stretching vibration), 1469, 1398, 1104, 744 $cm^{-1}$ <Ultraviolet-Visible Spectroscopic Analysis>

Absorption wavelength: 317, 371, 697 nm

It was confirmed from the above results that the green solid produced in Example 13 is a zinc tetra(tetrahydroquinoxalinediono) porphyrazine compound represented by formula (39) below.

[Chem. 28]

(39)

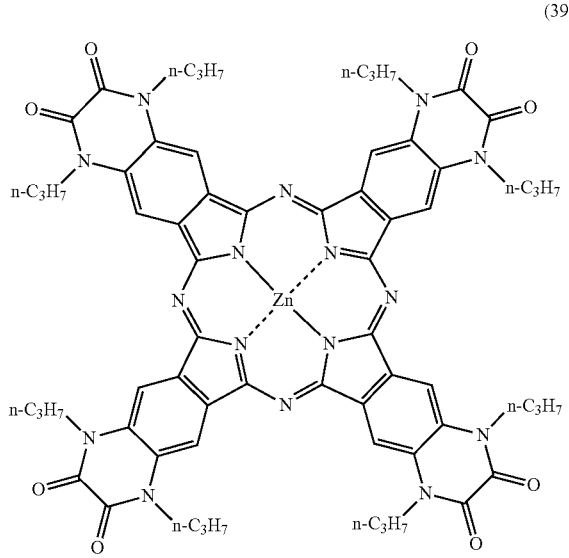

[Chem. 29]

(40)

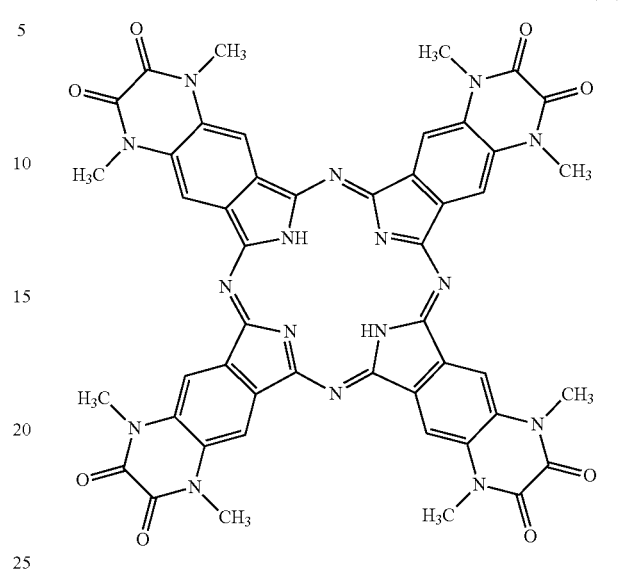

Example 14

Synthesis of phthalocyanine Compound Having methyl Groups as all of $R^1$ to $R^8$ in the General Formula (1-2) (n=2)

First, 1.00 parts by mass of the dicyanotetrahydroquinoxalinedione compound (24) produced in Synthesis Example 5 and 0.64 parts by mass of DBU were added to 8.15 parts by mass of 1-pentanol, and the resultant mixture was heated under reflux for 9 hours while being stirred. The reaction solution was cooled to 700° C. or less, and then the precipitated solid was filtered off. The resultant crude product was washed in order with hot methanol, hot acetone, hot N,N-dimethylformamide, and methanol to produce, as a green solid, 0.63 parts by mass (yield 63%) of the target phthalocyanine compound.

With respect to the compound produced as described above, FD/MS analysis, infrared spectroscopic analysis by a KBr disk method, and ultraviolet-visible spectroscopic analysis in a sulfuric acid solution were conducted to obtain analytical results described below.

<FD/MS Analysis> m/z=962 M+

<Infrared Spectroscopic Analysis>

1666 (C=O stretching vibration), 1464, 1384, 1116, 743 cm$^{-1}$

<Ultraviolet-Visible Spectroscopic Analysis>

Absorption wavelength: 336, 776, 819 nm

It was confirmed from the above results that the green solid produced in Example 14 is a metal-free tetra(tetrahydroquinoxalinediono)porphyrazine compound represented by formula (40) below.

(Measurement of Color Properties)

First, 0.3 parts by mass of the phthalocyanine compound synthesized in each of the examples was dispersed in 2.0 parts by mass of vanish using a rosin-modified phenol resin. The resultant coloring composition was drawn down on white paper to measure color properties with a spectrophotometer (Spectro Eye manufactured by Getrag Macbeth Corporation). The obtained results are shown in Table 1.

(Light Source D65 with 2-Degree Field of View)

in Table 1, C* represents chroma, and h represents a hue angle. Each of the synthesized compounds had a green hue.

TABLE 1

| Compound No. | C* | h | Hue |
| --- | --- | --- | --- |
| (27) | 47.7 | 147 | Green |
| (29) | 62.1 | 150 | Green |
| (30) | 62.0 | 152 | Green |
| (31) | 31.6 | 172 | Blue-green |
| (32) | 56.0 | 123 | Yellow-green |
| (33) | 50.8 | 147 | Green |
| (34) | 51.8 | 152 | Green |
| (35) | 59.5 | 155 | Green |
| (36) | 51.5 | 153 | Green |
| (38) | 50.8 | 152 | Green |
| (39) | 49.4 | 151 | Green |
| (40) | 36.4 | 136 | Green |

Example 15

Pigmentation

First, 0.50 parts by mass of the phthalocyanine compound (29) produced in Example 3 was ground together with 1.50 parts by mass of sodium chloride and 0.75 parts by mass of diethylene glycol. Then, the resultant mixture was poured into 600 parts by mass of hot water and stirred for 1 hour. A water-insoluble substance was filtered off, well washed with hot water, and then dried at 80° C. under reduced pressure to form a pigment. The pigment had a particle diameter of 300 nm or less and an average length/width ratio of particles of less than 3.

A baked coating film drawdown test and chemical resistance test were conducted using the resulting green pigment of the phthalocyanine compound (29).

<Baked Coating Film Drawdown Test>

First, 4 parts by mass of the green pigment of the phthalocyanine compound (29), 10 parts by mass of a mixed resin containing 70% of alkyd resin ("BECKOSOL J-524-IM-60" manufactured by DIC Corporation) and 30% of melamine resin ("SUPER BECKAMINE G-821-60" manufactured by DIC Corporation), 7 parts by mass of xylene, and 3 parts by mass of n-butanol were dispersed for 2 hours with a paint conditioner using glass beads as a medium. Then, 50 parts by mass of acryl melamine resin was added to the resultant dispersion, and the mixture was further mixed with a paint conditioner for 5 minutes, producing a green coloring composition.

The resultant green coloring composition was applied to a polyester film using an applicator and baked at 130° C. for 30 minutes. The resulting coating film has a glossy clear green color.

Figure 5:
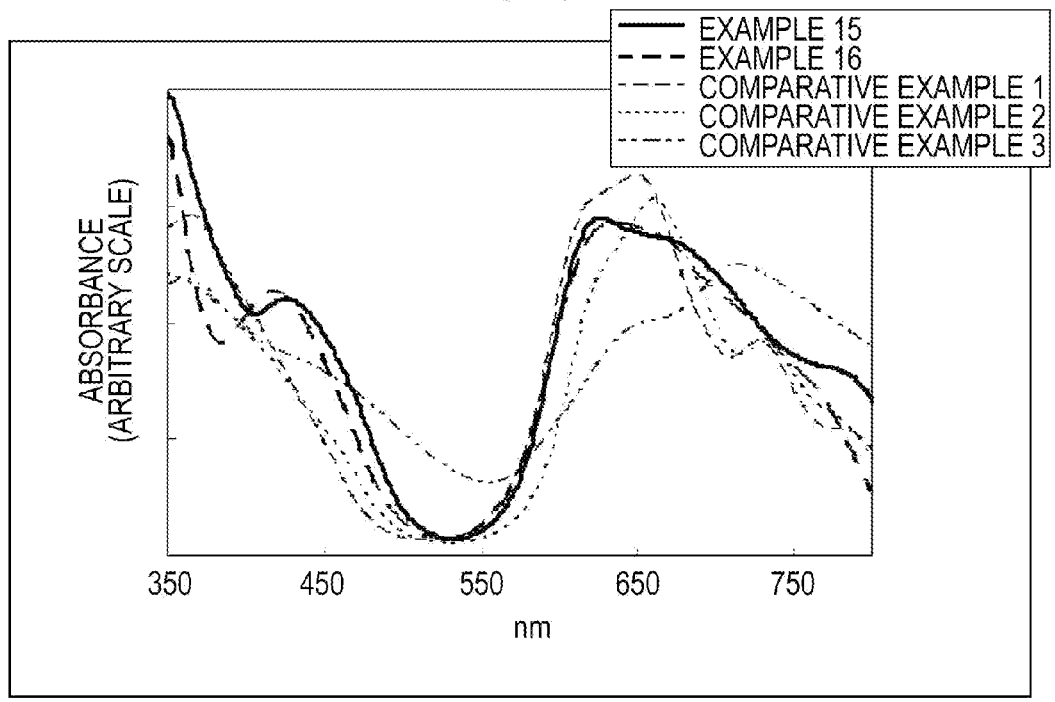
FIG. 5 shows optical absorption spectra of baked coating films formed in baked coating film drawdown tests in Examples 15 and 16 and Comparative Examples 1 to 3 of the present invention.
Figure 6:
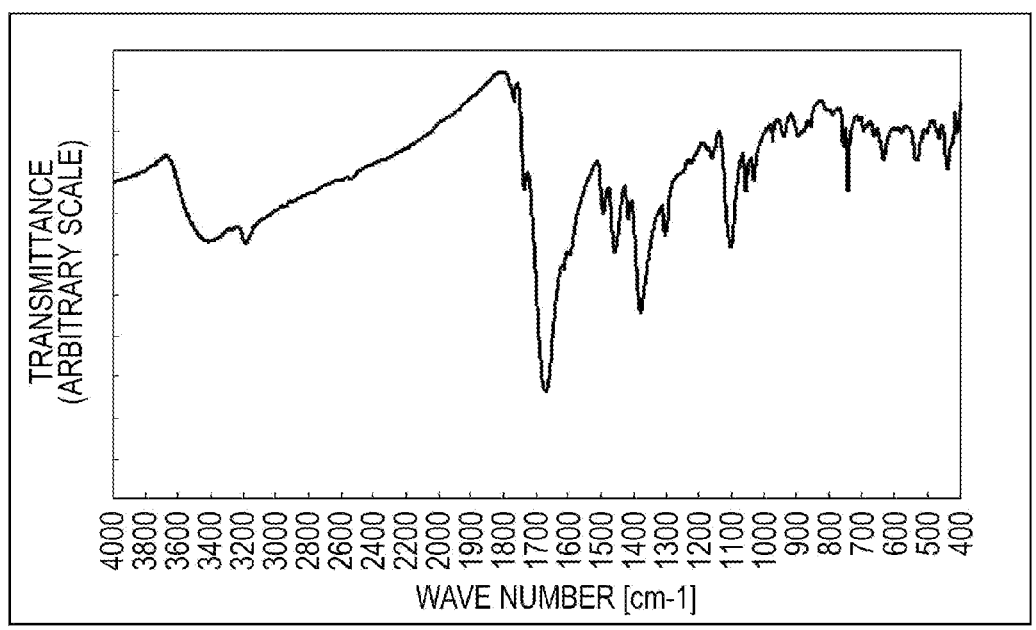
FIG. 6 shows an infrared spectrum of compound (36).
Figure 7:
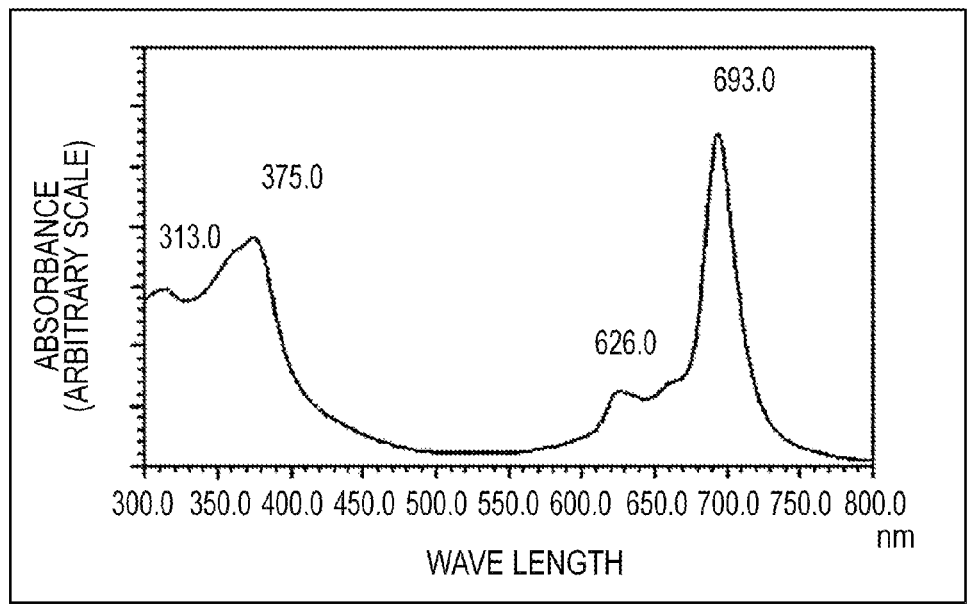
FIG. 7 shows an ultraviolet-visible spectrum of compound (36) in N,N-dimethylformamide.
Figure 8:
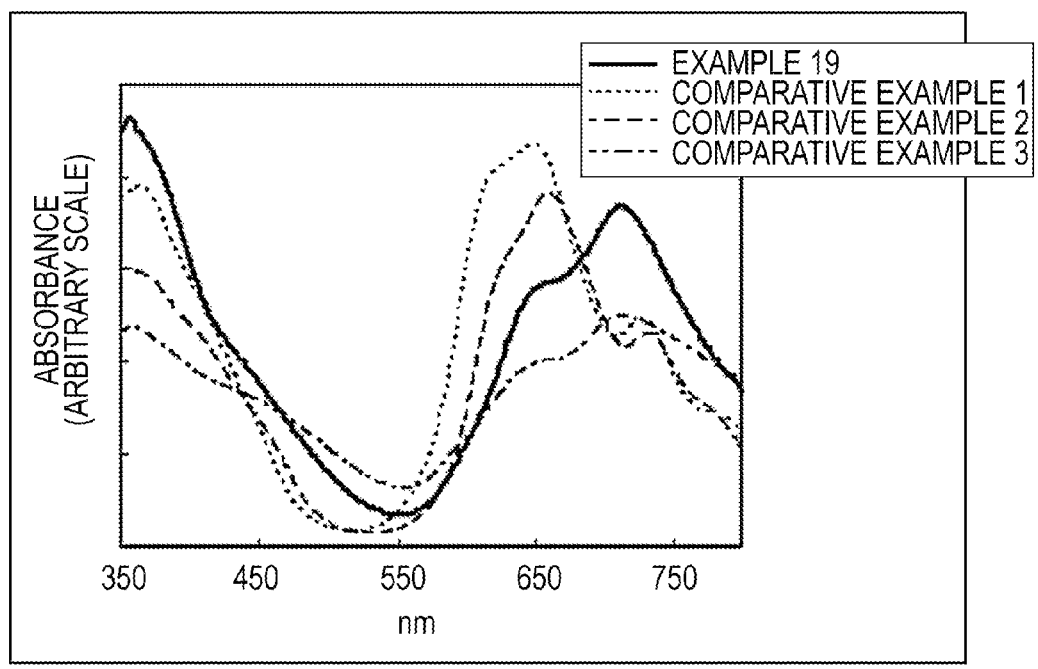
FIG. 8 shows optical absorption spectra of baked coating films formed in baked coating film drawdown tests in Example 19 and Comparative Examples 1 to 3 of the present invention.

For the coating film produced as described above, an ultraviolet-visible spectrum and color properties were measured using a spectrophotometer (using "UV-2450" manufactured by Shimadzu Corporation). The absorption wavelength of the coating film is shown in Table 2 below, and the measurement results of color properties are shown in Table 4. The optical absorption spectrum obtained by the measurement is shown in FIG. 5

<Chemical Resistance Test>

In a container with a cover, 1 part by mass of the green pigment of the phthalocyanine compound (29) and 20 parts by mass of an organic solvent or acid described in Table 1 were added, and the mixture was shaken for 30 seconds in the closed container and then allowed to stand for 15 minutes. Then, the mixture was again shaken for 30 seconds, allowed to stand for 30 minutes, and then filtered. Coloring of the filtrate was evaluated by visual observation on the basis of the following criteria.

Good: No coloring of filtrate was observed
Poor: Coloring of filtrate was observed Example 16

A baked coating film drawdown test and chemical resistance test were conducted by the same methods as in Example 15 except that the phthalocyanine compound (30) produced in Example 4 was used as a green pigment in place of the green pigment of the phthalocyanine compound (29).

Example 17

A baked coating film drawdown test and chemical resistance test were conducted by the same methods as in Example 15 except that the phthalocyanine compound (33) produced in Example 7 was used as a green pigment in place of the green pigment of the phthalocyanine compound (29).

Example 18

A baked coating film drawdown test and chemical resistance test were conducted by the same methods as in Example 15 except that the phthalocyanine compound (35) produced in Example 9 was used as a green pigment in place of the green pigment of the phthalocyanine compound (29).

Example 19

A baked coating film drawdown test and chemical resistance test were conducted by the same methods as in Example 15 except that the phthalocyanine compound (36) produced in Example 10 was used as a green pigment in place of the green pigment of the phthalocyanine compound (29).

Comparative Example 1

A baked coating film drawdown test and chemical resistance test were conducted by the same methods as in Example 15 except that chlorinated copper phthalocyanine pigment ("Fastogen Green S", C. I. Pigment Green 7, manufactured by DIC Corporation) was used in place of the green pigment of the phthalocyanine compound (29).

Comparative Example 2

A baked coating film drawdown test and chemical resistance test were conducted by the same methods as in Example 15 except that brominated copper phthalocyanine pigment ("Fastogen Green 2YK-CF", C. I. Pigment Green 36, manufactured by DIC Corporation) was used in place of the green pigment of the phthalocyanine compound (29).

Comparative Example 3

A baked coating film drawdown test was conducted by the same method as in Example 15 except that a green pigment of a phthalocyanine compound represented by formula (41) below and synthesized by the method described in Patent Literature 3 was used in place of the green pigment of the phthalocyanine compound (29).

[Chem. 30]

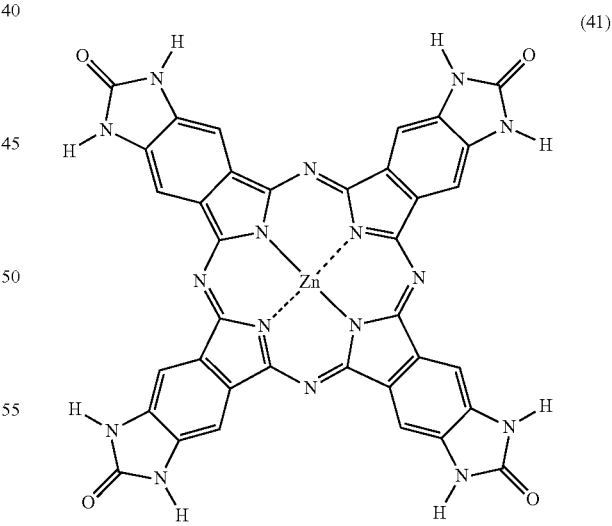

(41)

The test results of the green pigments of Examples 15 to 19 and Comparative Examples 1 to 3 are shown in Table 2 (Examples) and Table 3 (Comparative Examples). In Table 1, in the item "Halogen free", a halogen-free pigment is denoted by "Yes", and a non-halogen-free pigment" is denoted by "No".

TABLE 2

| Compound | Example 15 (29) | Example 16 (30) | Example 17 (33) | Example 18 (35) | Example 19 (36) |
|---|---|---|---|---|---|
| Halogen free | Yes | Yes | Yes | Yes | Yes |
| Hue | Green | Green | Green | Green | Green |
| Absorption wavelength of baked coating film (nm) | 425 627 | 418 636 | 426 649 700 | 418 628 668 | 352 712 |
| Maximum transmission wavelength of baked coating film (nm) | 533 | 528 | 543 | 525 | 552 |
| Chemical resistance test | | | | | |
| Methanol | Good | Good | Good | Good | Good |
| Acetone | Good | Good | Good | Good | Good |
| Ethyl acetate | Good | Good | Good | Good | Good |
| Xylene | Good | Good | Good | Good | Good |
| 2 mass % hydrochloric acid | Good | Good | Good | Good | Good |

TABLE 3

| Compound | Comparative Example 1 Chlorinated copper phthalocyanine | Comparative Example 2 Brominated copper phthalocyanine | Comparative Example 3 Compound (41) |
|---|---|---|---|
| Halogen free | No | No | Yes |
| Hue | Bluish green | Green | Dull green |
| Absorption wavelength of baked coating film (nm) | 365 649 | 660 | 358 660 714 |
| Maximum transmission wavelength of baked coating film (nm) | 519 | 532 | 555 |
| Chemical resistance test | | | |
| Methanol | Good | Good | Good |
| Acetone | Good | Good | Good |
| Ethyl acetate | Good | Good | Good |
| Xylene | Good | Good | Good |
| 2 mass % hydrochloric acid | Good | Good | Good |

The results shown in Table 3 reveal that the phthalocyanine compound of the present invention can be used as a halogen-free clear green pigment and has high chemical resistance to organic solvents and acids in the same level as chlorinated copper phthalocyanine and brominated copper phthalocyanine pigments which are known as existing green pigments with high chemical resistance.

TABLE 4

| | L* | a* | b* | C* |
|---|---|---|---|---|
| Example 15 | 81.3 | −74.1 | 38.4 | 83.5 |
| Example 16 | 77.2 | −84.4 | 37.3 | 92.3 |
| Example 17 | 77.6 | −73.1 | 43.9 | 85.3 |
| Example 18 | 78.8 | −87.5 | 45.2 | 98.5 |
| Example 19 | 74.7 | −51.9 | 46.7 | 69.8 |
| Comparative Example 1 | 74.2 | −88.2 | 17.8 | 90.0 |
| Comparative Example 2 | 79.8 | −78.5 | 39.6 | 87.9 |
| Comparative Example 3 | 78.4 | −24.2 | 20.5 | 31.7 |

(CIE Color Space Values with C Light Source and 2-Degree Field of View)

The results shown in Table 4 reveal that the phthalocyanine compound of the present invention is significantly improved in chroma (C*) as compared with the compound (41) of Comparative Example 3. It is also found that the compounds (29), (30), and (35) have a yellowish green hue close to that of brominated copper phthalocyanine.

INDUSTRIAL APPLICABILITY

A phthalocyanine compound of the present invention exhibits a clear green color and is halogen-free, and is thus useful as a green pigment for coloring materials such as a coating material, plastic, a printing ink, rubber, leather, textile printing, a color filter, a jet ink, a heat-transfer ink, etc.

The invention claimed is:
1. A phthalocyanine compound represented by general formula (1-1) or (1-2).

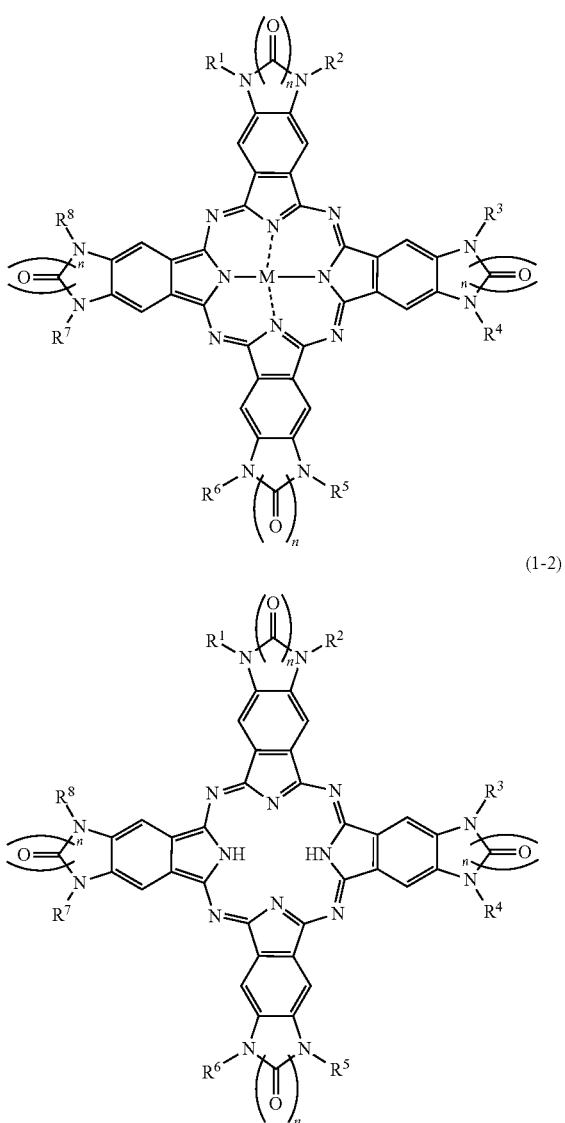

wherein
1) when n=1, $R^1$ to $R^8$ each independently represent an alkyl group having 1 to 6 carbon atoms, or an aralkyl group having 7 to 9 carbon atoms, and
2) when n=2, $R^1$ to $R^8$ each independently represent a hydrogen atom, an alkyl group having 1 to 6 carbon atoms, or an aralkyl group having 7 to 9 carbon atoms, and M in the general formula (1-1) represents a divalent to tetravalent metal atom and the metal atom may be oxidized.

2. The phthalocyanine compound according to claim 1, wherein the divalent to tetravalent metal atom represented by M in the general formula (1-1) is copper or zinc.

3. The phthalocyanine compound according to claim 1, wherein in the general formula (1-1) or general formula (1-2), $R^1$ to $R^8$ are each independently an alkyl group having 1 to 4 carbon atoms.

4. A phthalonitrile compound represented by general formula (2),

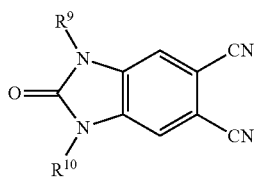

(2)

where $R^9$ and $R^{10}$ each independently represent an alkyl group having 1 to 6 carbon atoms, or an aralkyl group having 7 to 9 carbon atoms.

5. A phthalonitrile compound represented by general formula (3),

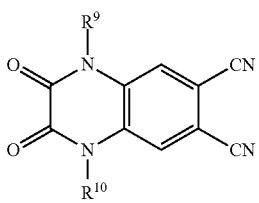

(3)

where $R^9$ and $R^{10}$ each independently represent an alkyl group having 1 to 6 carbon atoms, or an aralkyl group having 7 to 9 carbon atoms.

6. A method for producing the phthalocyanine compound according to claim 1, the method comprising thermally condensing the phthalonitrile compound alone represented by the general formula (2) or (3)

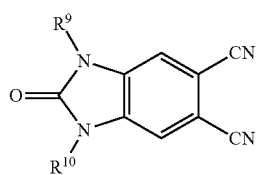

(2)

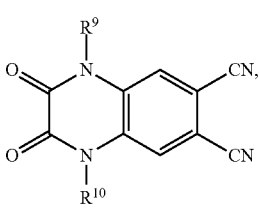

(3)

or a mixture thereof with a metal salt corresponding to the divalent to tetravalent metal atom represented by M in the general formula (1-1).

7. A coloring composition comprising the phthalocyanine compound according to claim 1 and a synthetic resin.

* * * * *